US007575921B2

(12) United States Patent
Vacanti et al.

(10) Patent No.: US 7,575,921 B2
(45) Date of Patent: Aug. 18, 2009

(54) SPORE-LIKE CELLS AND USES THEREOF

(75) Inventors: Martin P. Vacanti, Westborough, MA (US); Charles A. Vacanti, Uxbridge, MA (US)

(73) Assignee: VBI Technologies, L.L.C., Houston, TX (US)

(*) Notice: Subject to any disclaimer, the term of this patent is extended or adjusted under 35 U.S.C. 154(b) by 298 days.

(21) Appl. No.: 10/462,034

(22) Filed: Jun. 13, 2003

(65) Prior Publication Data
US 2004/0057942 A1    Mar. 25, 2004

Related U.S. Application Data

(63) Continuation of application No. 09/476,047, filed on Dec. 30, 1999, now abandoned.

(51) Int. Cl.
C12N 5/06    (2006.01)
A61K 48/00   (2006.01)
(52) U.S. Cl. .................... 435/325; 424/93.21
(58) Field of Classification Search ............ None
See application file for complete search history.

(56) References Cited

U.S. PATENT DOCUMENTS

| | | | |
|---|---|---|---|
| 4,060,081 A | 11/1977 | Yannas et al. |
| 4,191,747 A | 3/1980 | Scheicher |
| 4,846,835 A | 7/1989 | Grande |
| 4,997,443 A | 3/1991 | Walthall et al. |
| 5,041,138 A | 8/1991 | Vacanti et al. |
| 5,071,644 A | 12/1991 | Viegas et al. |
| 5,082,670 A | 1/1992 | Gage et al. |
| 5,126,141 A | 6/1992 | Henry |
| 5,192,326 A | 3/1993 | Bao et al. |
| 5,277,911 A | 1/1994 | Viegas et al. |
| 5,292,516 A | 3/1994 | Viegas et al. |
| 5,292,655 A | 3/1994 | Wille, Jr. et al. |
| 5,294,446 A | 3/1994 | Schlameus et al. |
| 5,298,260 A | 3/1994 | Viegas et al. |
| 5,300,295 A | 4/1994 | Viegas et al. |
| 5,306,501 A | 4/1994 | Viegas et al. |
| 5,318,780 A | 6/1994 | Viegas et al. |
| 5,405,366 A | 4/1995 | Fox et al. |
| 5,410,016 A | 4/1995 | Hubbell et al. |
| 5,443,950 A | 8/1995 | Naughton et al. |
| 5,512,600 A | 4/1996 | Mikos et al. |
| 5,514,378 A | 5/1996 | Mikos et al. |
| 5,529,914 A | 6/1996 | Hubbell et al. |
| 5,567,612 A | 10/1996 | Vacanti et al. |
| 5,575,815 A | 11/1996 | Slepian et al. |
| 5,578,485 A | 11/1996 | Naughton et al. |
| 5,589,376 A | 12/1996 | Anderson et al. |
| 5,593,974 A | 1/1997 | Rosenberg et al. |
| 5,667,778 A | 9/1997 | Atala |
| 5,696,175 A | 12/1997 | Mikos et al. |
| 5,709,854 A | 1/1998 | Griffith-Cima et al. |
| 5,716,404 A | 2/1998 | Vacanti et al. |
| 5,736,372 A | 4/1998 | Vacanti et al. |
| 5,750,376 A | 5/1998 | Weiss et al. |
| 5,753,506 A | 5/1998 | Johe |
| 5,759,830 A | 6/1998 | Vacanti et al. |
| 5,762,926 A | 6/1998 | Gage et al. |
| 5,770,193 A | 6/1998 | Vacanti et al. |
| 5,770,417 A | 6/1998 | Vacanti et al. |
| 5,780,300 A | 7/1998 | Artavanis-Tsakonas et al. |
| 5,786,216 A | 7/1998 | Dionne et al. |
| 5,795,790 A | 8/1998 | Schinstine et al. |
| 5,804,178 A | 9/1998 | Vacanti et al. |
| 5,827,735 A | 10/1998 | Young et al. |
| 5,830,651 A | 11/1998 | Cauley et al. |
| 5,834,029 A | 11/1998 | Bellamkonda et al. |
| 5,851,832 A | 12/1998 | Weiss et al. |
| 5,855,610 A | 1/1999 | Vacanti et al. |
| 5,994,754 A | 11/1999 | Hayashi et al. |
| 2003/0008351 A1* | 1/2003 | Deisher et al. ............. 435/69.1 |

FOREIGN PATENT DOCUMENTS

| | | |
|---|---|---|
| EP | 0 361 957 | 4/1990 |
| WO | WO 93/16687 | 2/1993 |
| WO | WO 93/24627 | 12/1993 |
| WO | WO 94/25079 | 11/1994 |
| WO | WO 94/25080 | 11/1994 |
| WO | WO 96/40304 | 12/1996 |
| WO | WO 97/41208 | 11/1997 |
| WO | WO 98/23761 | 6/1998 |
| WO | WO 98/30678 | 7/1998 |

OTHER PUBLICATIONS

Colussi, PA and P Orlean Yeast 13:139-150, 1997.*
Wolk, CP Bacteriol Rev 37(1):32-101, 1973.*
Guidry, C. Invest Ophthalmol Vis Sci 37(5):abstract, 1996.*
Zuk et al. Molecular Biology of the Cell 13:4279-4295, 2002.*
Burke et al., Ann. Surg. 194:413-428, 1981.
Cornelius et al., "In Vitro-Generation of Islets in . . . " Hormone Metabol. Res., 29:271-277, 1997.
Craig et al., "In Vivo Growth Factor Expansion of Endogenous Subependymal Neural Precursor Cell Populations in the Adult Mouse Brain," The Journal Of Neuroscience, 16:2649-2658, 1996.
Davis et al., "A Self-Renewing Multipotential Stem Cell in Embryonic Rat Cerebral Cortex," Nature, 372:263-269, 1994.
Farriol et al., "Epidermal growth factor excretion in burned rats" Burns 20:496-498, 1994.
Frederiksen et al., "Proliferation and Differentiation of Rat Neuroepithelial Precursor Cells In Vivo," The Journal Of Neuroscience, 8:1144-1151, 1988.
Ferringa et al., "Regeneration of Corticospinal Axons in the Rat," Annals Of Neurology, 2:315-321, 1977.

(Continued)

*Primary Examiner*—Deborah Crouch
*Assistant Examiner*—Marcia S Noble
(74) *Attorney, Agent, or Firm*—Pabst Patent Group LLP

(57) ABSTRACT

Highly undifferentiated spore-like cells can be isolated from many different tissues and bodily fluids and used to treat a wide variety of disorders.

8 Claims, 18 Drawing Sheets

OTHER PUBLICATIONS

Gage et al., "Survival and Differentiation of Adult Neuronal Progenitor Cells Transplanted to the Adult Brain," Proc. Natl. Acad. Sci. USA, 92:11879-11883, 1995.

Hansbrough, "Current Status of Skin Replacement for Coverage of . . . " J. Trauma, 30(12):S155-S162, 1992.

Houle et al., "Bridging a Complete Transection Lesion of Adult Rat Spinal Cord with Growth Factor-Treated Nitrocellulose Implants," Journal Of Neural Transplantation & Plasticity, 5:115-124, 1994.

Lachyanker et al., "Embryonic Precursor Cells that Express Trk Receptors: Induction of Different Cell Fates by NGF, BDNF, NT-3, and CNTF," Experimental Neurology, 144:350-360, 1997.

Langer et al., "Tissue Engineering," Science 260:920-926, 1993.

Lindsell et al., "Jagged: A Mammalian Ligand . . . " Cell 80:909-917, 1995.

Moore et al., "Vascular function and tissue injury in murine skin . . . " Br. J. Cancer 66:1037-1043, 1992.

Morshead et al., "Neural Stem Cells in the Adult Mammalian Forebrain: A Relatively Quiescent Subpopulation of Subependymal Cells," Neuron, 13:1071-1082, 1994.

Nerem, "Cellular Engineering," Ann. Biomed. Eng. 19:529, 1991.

Raszka et al., "The Use of Hyaluronidase . . . " J. Perinatol. 10:146-149, 1990.

Ray et al., "Proliferation, Differentiation, and Long-Term Culture of Primary Hippocampal Neurons," Proc. Natl. Acad. Sci. USA, 90:3602-3606, 1993.

Ray et al., "Spinal Cord Neuroblasts Proliferate in Response to Basic Fibroblast Growth Factor," The Journal Of Neuroscience, 14:3548-3564, 1994.

Reynolds et al., "Clonal and Population Analyses Demonstrate that an EGF-Responsive Mammalian Embryonic CNS Precursor is a Stem Cell," Developmental Biology, 175:1-13, 1996.

Reynolds et al., "Generation of Neurons and Astrocytes from Isolated Cells of the Adult Mammalian Central Nervous System," Science, 255:1707-1710, 1992.

Reynolds et al., "A Multipotent EGF-Responsive Striatal Embryonic Progenitor Cell Produces Neurons and Astrocytes," The Journal Of Neuroscience, 12:4565-4574, 1992.

Shihabuddin et al., "FGF-2 Is Sufficient to Isolate . . . " Exp. Neurol. 148-577-586, 1997.

Shihabuddin et al., "The Adult CNS Retains the Potential to Direct Region-Specific Differentiation of a Transplanted Neuronal Precursor Cell Line," The Journal Of Neuroscience, 15:6666-6678, 1995.

Shihabuddin et al., "Induction of Mature Neuronal Properties in Immortalized Neuronal Precursor Cells Following Grafting into the Neonatal CNS," Journal Of Neurocytology, 25:101-111, 1996.

Stanton et al., "The Growth of Chondrocytes Using Gelfoam as a Biodegradable Scaffold," Journal Of Materials Science: Materials In Medicine 6:739-744, 1996.

Suhonen et al., "Differentiation of Adult Hippocompus-Derived Progenitors into Olfactory Neurons in Vivo," Nature, 383:624-627, 1996.

Taylor et al., "Widespread Engraftment of Neural Progenitor and Stem-Like Cells Throughtout the Mouse Brain," Transplantation Proceedings, 29:845-847, 1997.

Weiss et al., "Multipotent CNS Stems Cells are Present in the Adult . . . " J. Neurosci. 16:7599-7609, 1996.

Yannas et al., "Wound Tissue Can Utilize . . . " Science 215:174-176, 1982.

* cited by examiner

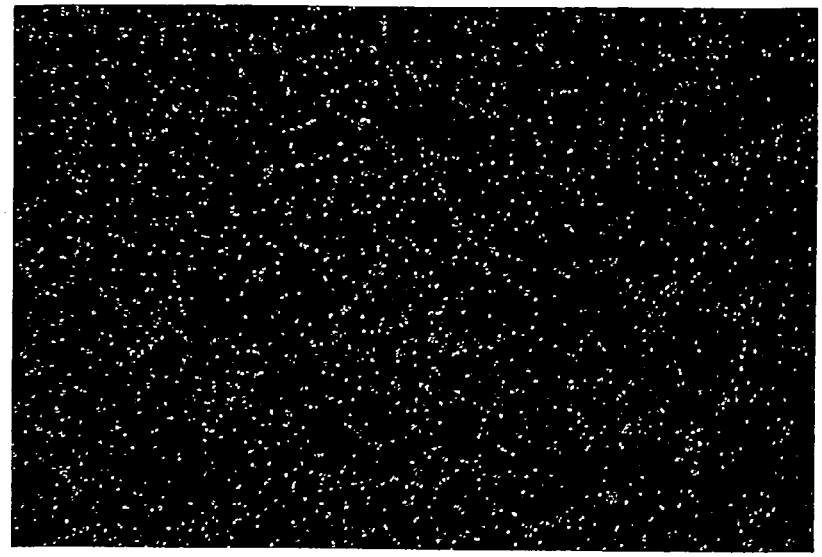
FIG. 8A
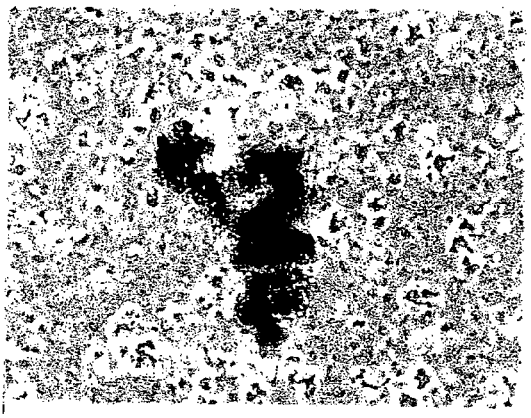 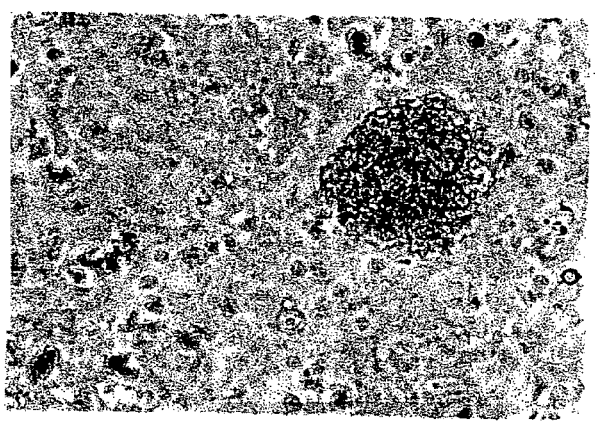
FIG. 8B          FIG 8C

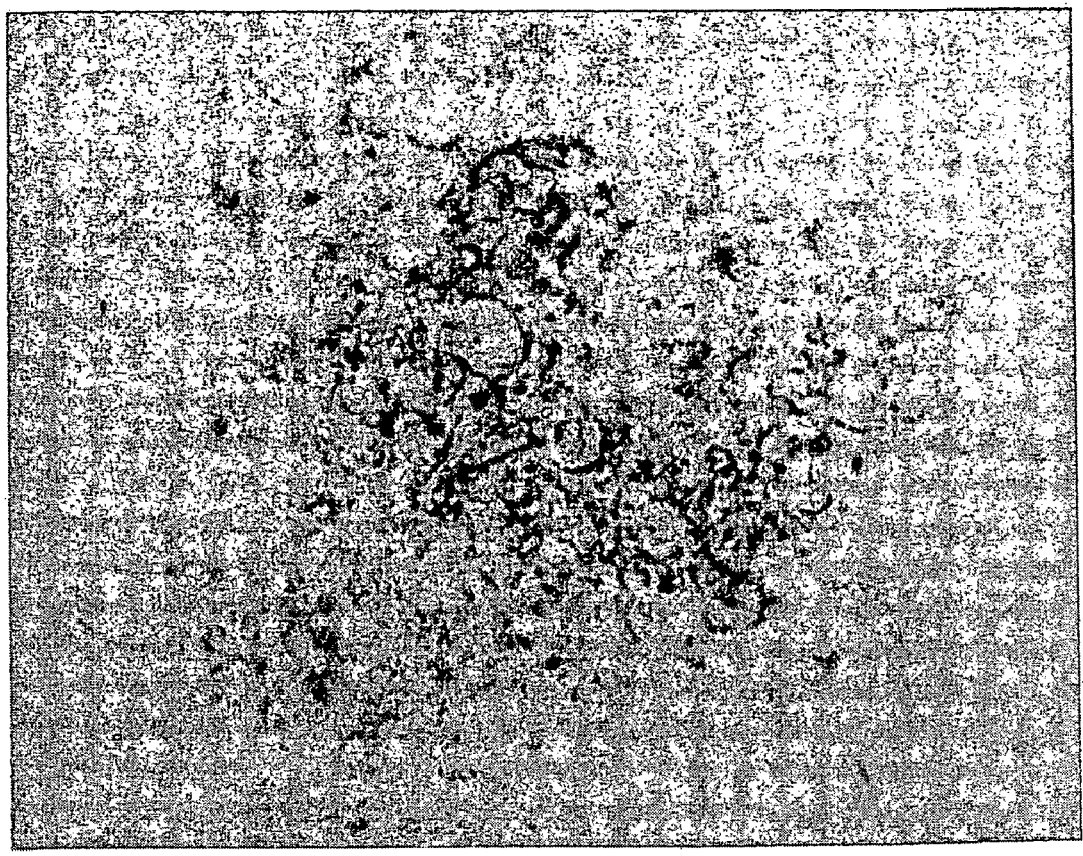
FIG. 8D
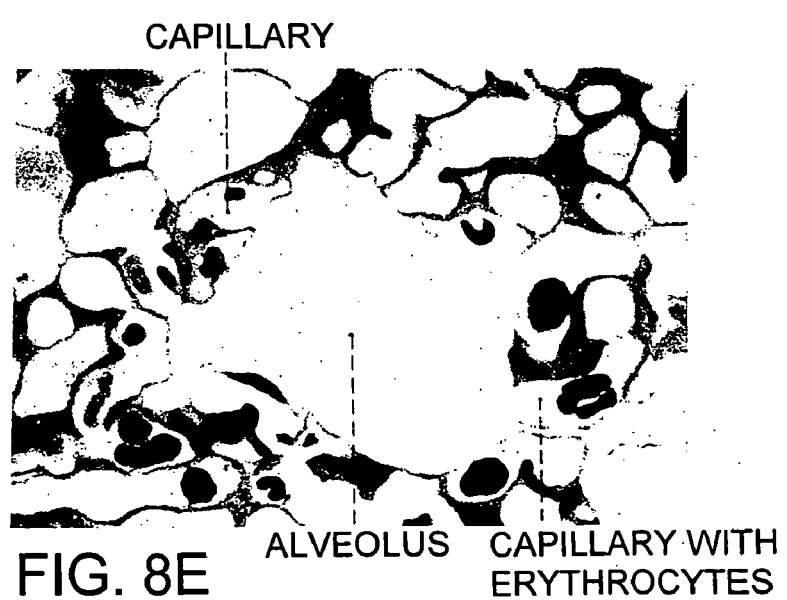
FIG. 8E   ALVEOLUS   CAPILLARY WITH ERYTHROCYTES
CAPILLARY

SPORE-LIKE CELLS AND USES THEREOF

This application is a continuation (and claims the benefit of priority under 35 USC 120) of U.S. application Ser. No. 09/476,047, filed Dec. 30, 1999 now abandoned. The disclosure of the prior application is considered part of (and is incorporated by reference in) the disclosure of this application.

FIELD OF THE INVENTION

The invention relates to compositions and methods for tissue engineering and cell therapies.

BACKGROUND OF THE INVENTION

Every year, millions of people suffer tissue loss or end-stage organ failure (see, e.g., Langer and Vacanti, *Science* 260:920-926, 1993). When possible, physicians treat this loss or failure by transplanting organs from one individual to another, performing surgical reconstruction, or using mechanical devices such as kidney dialyzers. Although these therapies have saved and improved countless lives, they are imperfect solutions.

Transplantation is severely limited by critical donor shortages, which worsen every year, and surgical reconstruction can cause long-term problems. For example, colon cancers often develop after surgical treatment of incontinence that directs urine into the colon. Mechanical devices not only inconvenience the patient, but also perform organ function imperfectly. Thus, they cannot prevent progression of the patient's disorder.

A new alternative to the measures described above is tissue engineering, an interdisciplinary field that applies engineering and life science principles to the development of biological substitutes that maintain, improve, or restore tissue function (*Tissue Engineering*, R. Skalak and C. F. Fox, Eds., Alan R. Liss, New York, N.Y., 1988; Nerem, *Ann. Biomed. Eng.* 19:529, 1991). Three general strategies have been adopted for the creation of new tissue. The first employs isolated cells or cell substitutes. This approach avoids the complications of surgery, allows replacement of only those cells that supply the needed function, and permits manipulation of cells before they are administered to a patient. However, the cells do not always maintain their function in the recipient and can evoke an immune response that results in their destruction. The second approach employs tissue-inducing substances. For this approach to succeed, appropriate signal molecules, such as growth factors, must be purified and appropriately targeted to the affected tissue. The third approach employs cells placed on or within matrices. In closed systems, these cells are isolated from the body by a membrane that is permeable to nutrients and wastes, but impermeable to harmful agents such as antibodies and immune cells. Closed systems can be implanted or used as extra-corporeal devices. In open systems, cell-containing matrices are implanted and become incorporated into the body. The matrices are fashioned from natural materials such as collagen or from synthetic polymers. Immunological rejection may be prevented by immunosuppressive drugs or by the use of autologous cells.

SUMMARY OF THE INVENTION

The invention is based on the discovery of highly undifferentiated spore-like cells, which can be isolated from many different tissues and bodily fluids and used to treat a wide variety of disorders. For example, spore-like cells can be used to reengineer damaged or diseased tissue, to augment existing tissue, to create new tissue, or to otherwise improve the condition of a patient who is suffering from a disorder that is amenable to treatment by a cell- or gene-based therapy.

For example, spore-like cells that differentiate into various skin cells can be used to repair skin damaged by physical, thermal, or chemical trauma. As other examples, spore-like cells that differentiate into insulin-secreting cells can be used to treat diabetes; spore-like cells that differentiate into α-galactosidase A-expressing cells can be used to treat Fabry disease; and spore-like cells that differentiate into cells that express angiogenesis inhibiting factors, such as an endostatin, or other anti-tumor agents (e.g., tumor necrosis factor), can be used to treat cancer. Alternatively, or in addition, one can use spore-like cells that are engineered to secrete substances such as those described above. The cells can be made to express a wide variety of substances by genetic manipulation or exposure to factors that alter their course of differentiation.

Accordingly, the invention features isolated spore-like cells having the following characteristics. The cells are multipotent (i.e., they have the potential to differentiate into two or more cell types. For example, multipotent spore-like cells can differentiate into epithelial cells, keratinocytes, and melanocytes. The cell is also small, having a diameter of approximately one to seven microns (e.g., a diameter of one to two, two to four, three to five, or five to ten microns in diameter), and is tolerant of oxygen-deprivation. Viable spore-like cells can survive in low-oxygen environments (such as those that exist within the tissues of a deceased animal) for many hours (e.g., four, six, ten, twelve, or 24 hours or more). Spore-like cells are surrounded by an outer membrane that is rich in glycolipids and mucopolysaccharids. In fact, there are sufficient glycolipids and mucopolysaccharides that the cells appear to have one or more dark stripes when viewed by transmission electron microscopy. When the cells are exceedingly small (e.g., less than one micron, as described below) the stripes are not as obvious but can nevertheless be seen with a trained eye. Electron micrographs and histological stains for nucleic acids reveal that a large portion (e.g., at least about 50% and up to 90% or more) of the volume of a spore-like cell is comprised of nucleic acids.

Spore-like cells can be obtained from various tissues, organs, and bodily fluids. For example, spore-like cells can be isolated from bodily fluids (e.g., blood or cerebrospinal fluid) of a post-natal animal (e.g., a mammal) or from solid organs such as the heart (or other muscle types, such as smooth or skeletal muscle), intestine, bladder, kidney, liver, lung, adrenal gland, skin, retina, or pancreas.

The invention also features spore-like cells having a diameter of less than approximately one micron (e.g., one-tenth to one-fifth of a micron) in diameter. A great deal of the volume of these cells is also comprised of nucleic acids (e.g., at least about half the volume of the cell and up to more than 90% of the cell can consist of nuclear material).

In another aspect, the invention features a method for isolating spore-like cells, which is carried out by passing a tissue sample through a series of devices (e.g., size-exclusion devices such as pipettes or filters) having progressively smaller apertures (the smallest of which can be approximately 15μ). Smaller diameters (i.e., diameters smaller than 15μ) can also be used when more aggressive isolation is desired (i.e., when one desires fewer differentiated cells in the resulting culture). More aggressive isolation may be desired when one wishes to maintain the spore-like cells in their highly undifferentiated state. As described below, the conditions in which the cells are cultured can be such that their proliferation is encouraged and their differentiation is discouraged.

In another aspect, the invention features isolated cells that are non-terminally differentiated progeny of spore-like cells. Spore-like cells and their progeny (also referred to herein as progenitor cells) are non-terminally differentiated so long as they fail to express markers expressed by terminally differentiated cells (such as keratin, tyrosinase, glutamic acid, glutamate, citrulline, tricohyaline, filagrin, epinephrine, norepinephrine, acetylcholine, insulin, glucagon, dopamine, melanin granules, opsin, rhodopsin, collagen, serotonin, bile, bilirubin, estrogen, progesterone, testosterone, Thy-1.1, PKC-gamma, tyrosine hydroxylase or a cellular retinoic acid binding protein).

Spore-like cells and their progeny can be used in many ways. For example they can be used in conjunction with tissue engineering constructs (i.e., materials or devices used to reengineer damaged, diseased, or otherwise unhealthy tissue). These constructs can include support structures, such as a mesh, and a hydrogel. Together, the hydrogel and the spore-like cells of the invention form a hydrogel-spore-like cell composition. Similarly, a hydrogel combined with a progenitor cells forms a hydrogel-progenitor cell composition.

In another aspect, the invention features a method for generating an artificial tissue by, for example, combining hydrogel with a spore-like cell or the progeny of a spore-like cell. The hydrogel-cell compositions can be delivered into a permeable, biocompatible support structure. The hydrogel-cell compositions can be used to treat damaged tissue (e.g., a hydrogel-spore-like cell composition can be applied to the damaged tissue).

The invention also features methods of treating patients who have a disorder, such as a skin disorder, a tumor, or a disease, such as diabetes. The method is carried out, for example, by administering a spore-like cell or its progeny to the damaged region (e.g., the damaged region of the patient's skin, the area from which the tumor was ablated, or the pancreas). Systemic administration is also possible. The methods of the invention can be used to treat a patient who has a deficiency of functional cells in any of a wide variety of tissues, including the retina, intestine, bladder, kidney, liver, lung, nervous system, or endocrine system.

Spore-like cells and their progeny must originally be isolated from their natural environment (i.e., removed from a place where they reside within an animal) to fall within the present invention. Accordingly, an "isolated" spore-like cell can be one that is placed in cell culture, even temporarily. The term covers single, isolated spore-like cells and their progeny, as well as cultures of spore-like cells (and/or their progeny) that have been significantly enriched (i.e., cultures in which less than about 10% of the cells are fully differentiated cells).

The term "disorder" encompasses medical disorders, conditions, syndromes, illnesses, and diseases, regardless of their etiology. For example, a disorder amenable to treatment with the materials and methods described herein can be caused by trauma, a genetic defect, an infection, substance abuse, uncontrolled cellular proliferation, or a degenerative process (e.g., muscular atrophy). A given disorder is successfully treated when the symptoms of the disorder are alleviated and/or the underlying cause is eliminated or counteracted, either completely or partially.

A "hydrogel" is a substance formed when an organic polymer, which can be natural or synthetic, is set or solidified to create a three-dimensional, open-lattice structure that entraps molecules of water or other solutions to form a gel. Solidification can occur by aggregation, coagulation, hydrophobic interactions, cross-linking, or similar means. Preferably, the hydrogels used in conjunction with spore-like cells solidify so rapidly that the majority of the spore-like cells are retained at the application site. This retention enhances new cell growth at the application site. However, those of ordinary skill in the art will recognize that cellular retention is not always necessary. For example, retention is not necessary when treating a systemic disorder. The hydrogels are also biocompatible (e.g., they are not toxic to cells). The "hydrogel-cell composition" referred to herein is a suspension that includes a hydrogel and a spore-like cell or its progeny.

The invention has many advantages. For example, the compositions and methods described herein can be used to produce sufficient biological material for tissue engineering. This is not always possible when fully differentiated cells are used as the starting material. In addition, spore-like cells can differentiate into a greater variety of cell types than previously identified progenitor cells isolated from adult mammals. Thus, spore-like cells can be used to maintain or repair many, if not all, tissues and organs, including those (such as the retina) that have not been considered likely candidates for tissue engineering. The pluripotent nature of spore-like cells also allows more histologically complete development of any given tissue. For example, spore-like cells can be used to engineer skin that is pigmented and that contains adnexal structures (i.e., accessory structures or appendages such as hair follicles, sweat glands, sebaceous glands, nail beds, and specialized sensory receptors that allow us to sense pain, pressure, temperature, position, etc). The pigmentation and adnexal structures render the skin replacement a more visually appealing and functional replacement for natural, undamaged skin. Of course, disorders affecting the skin are only one of the many types of disorders that can be treated with spore-like cells. Analogous benefits will be apparent when systemic disorders or disorders affecting other organs (e.g., the pancreas, liver, or heart) are treated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflicting subject matter, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 4A-4C are shown at a magnification of 200×.

FIGS. 8A-8C are photographs of cells isolated from the lung of an adult rat; FIG. 8D is a photograph of cells in a culture initiated by spore-like cells obtained from an adult sheep lung; and FIG. 8E is a photograph of a semi-thin section of a feline lung. The newly isolated cells shown in FIG. 8A include undifferentiated spore-like cells. After six weeks in culture, alveolar-like cells can be seen (FIGS. 8B and 8C). After 30 days in culture, spore-like cells have formed alveolar-like structures (FIG. 8D) similar to those seen in the lungs of adult mammals (FIG. 8E).

FIGS. 10A and 10B). The islet-like structures were immunostained, which revealed insulin expression (FIG. 10C).

In FIG. 12A, the cells are viewed with phase contrast microscopy. In FIG. 12B, the cells are illuminated with fluorescent light following immunohistochemistry for nestin.

DETAILED DESCRIPTION

Figure 1A:
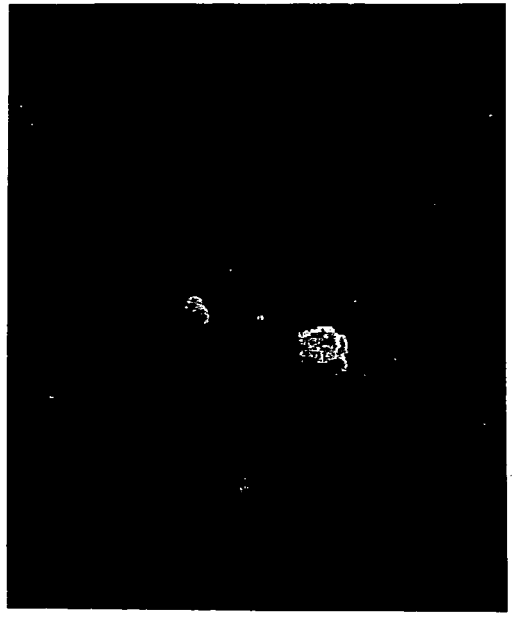
FIGS. 1A-1C are scanning electron micrographs of spore-like cells obtained from the liver of an adult rat. The cells are magnified 5,000× in FIGS. 1A and 1B, and 10,000× in FIG. 1C. The scale bars represent 1.0μ.
Figure 1B:
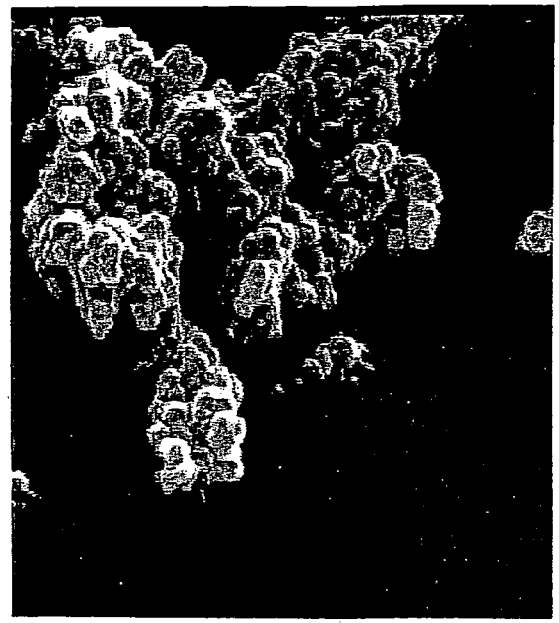
Figure 1C:
Figure 2A:
FIGS. 2A-2D are transmission electron micrographs of spore-like cells obtained from the liver of an adult rat and placed in culture for 12 days. The magnification in FIGS. 2A-2D is 25,000×, 39,000×, 17,000×, and 90,000× respectively.
Figure 2B:
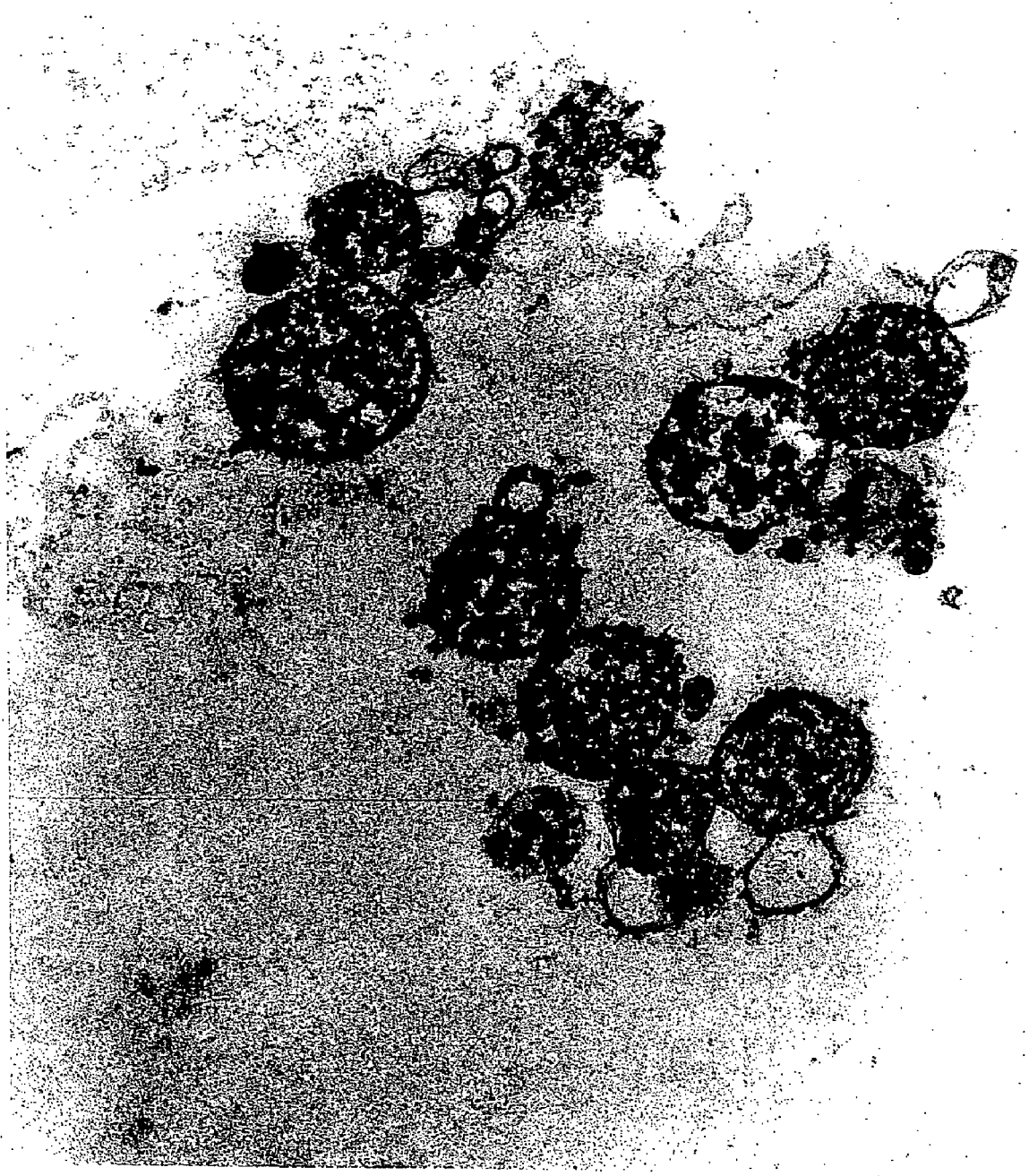
Figure 2C:
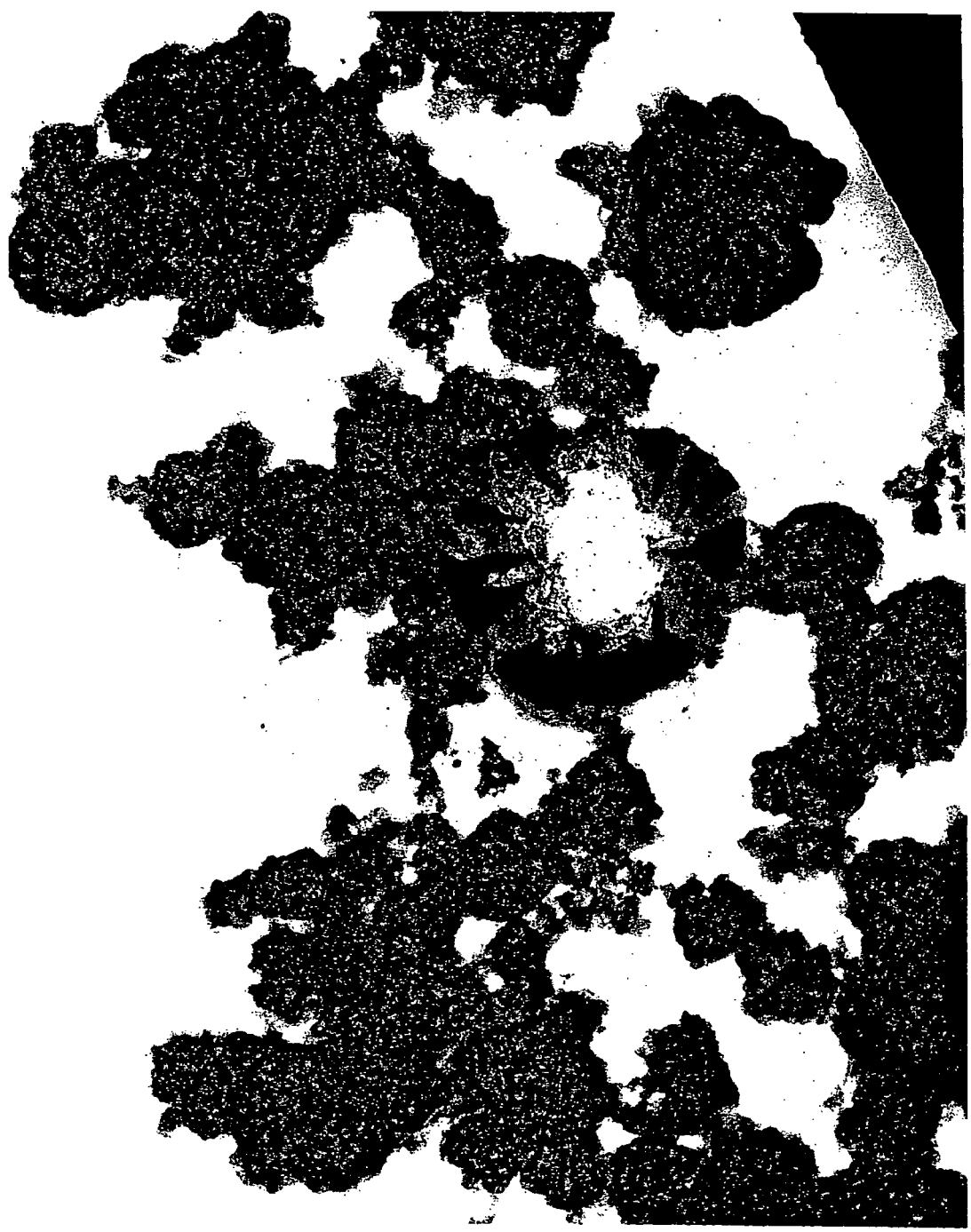
Figure 2D:

The present invention provides compositions and methods for repairing, replacing, or generating tissue or another biologically useful substance (e.g., a hormone, an enzyme, or an anti-angiogenic factor). The compositions include spore-like cells (e.g., mammalian spore-like cells), and can be administered to a patient by the methods described below or by way of existing tissue engineering or cell therapy procedures known to those of ordinary skill in the art.

When spore-like cells are used in cell therapies, they can be administered just as more differentiated cells have been administered. For example, when spore-like cells are used to treat diabetes, they can be administered just as mature insulin-expressing cells have been administered (e.g., by implantation under the renal capsule or within various implantable or extracorporeal devices). In fact, spore-like cells can be placed within a containment device and implanted, for example, within a patient's abdomen to treat a variety of disorders. This method of administration is particularly well suited for treating systemic disorders, such as those caused by an enzymatic imbalance. Implantation by way of containment devices is also useful when cells require protection from the patient's immune system.

Alternatively, as described below, spore-like cells can be combined with a liquid hydrogel that can be placed in a permeable, biocompatible support structure that is delivered to a patient (either before or after it is filled with the hydrogel-cell composition). As the hydrogel-cell composition fills the support structure, it assumes the structure's shape. When spore-like cells proliferate and differentiate to such an extent that they form new tissue, the support structure guides the shape of the developing tissue. For example, the support structure can be shaped as a bone (or a fragment thereof), a meniscus within a joint, an ear, an internal organ (or a portion thereof), or other tissue (e.g., the skin). However, the support structure need not be strictly fashioned after naturally occurring tissue in every case. For example, the support structure can be shaped in a way that simply facilitates delivery of spore-like cells to a patient. For example, the support structure can be shaped to fit under the renal capsule or within some other organ or cavity (e.g., the support structure can be shaped to lie within a portion of the gastrointestinal tract or to fill a space once occupied by tissue, such as the spaces created when a tumor is surgically removed or when a tissue has been destroyed following trauma, ischemia, or an autoimmune response).

In some instances, including instances where spore-like cells are administered in the course of cell or gene therapy, spore-like cells can be administered without containment devices, hydrogels, or support structures. It is well within the ability of one of ordinary skill in the art to determine when spore-like cells should be confined within a space dictated by a support structure and when they should not. For example, one of ordinary skill in the art would recognize that when treating respiratory distress syndrome (RDS) with spore-like cells that are made to secrete surfactant, or that differentiate into cells that secrete surfactant, the surfactant, which reduces surface tension within the alveoli, must be supplied locally.

Spore-like cells, and their progeny, and exemplary methods for their administration, are described below.

Spore-like Cells

Spore-like cells can be obtained from a donor (e.g., a member of an avian, reptilian, amphibian, or mammalian class). For example, mammalian spore-like cells can be isolated from a rodent, a rabbit, a cow, a pig, a horse, a goat, a sheep, a dog, a cat, a non-human primate, or, preferably, a human). Spore-like cells can be obtained from an animal even after it has reached adulthood. Because spore-like cells tolerate oxygen deprivation better than differentiated cells, viable spore-like cells can also be isolated from deceased animals, including animals that have been deceased for many hours (e.g., animals that have been deceased for 24 hours or more).

In addition, spore-like cells can be obtained from a variety of sources within a given donor. For example, spore-like cells can be obtained from bodily fluids (e.g., blood, saliva, or urine), and most, if not all, functional organs. Moreover, spore-like cells can be obtained from the patient who will be subsequently treated with those cells, from another person, or from an animal of a different species. In other words, autologous, allogenic, and xenogeneic spore-like cells can be obtained and used to treat human patients.

Regardless of the source from which they are obtained, spore-like cells can be placed in culture, and cell lines derived from spore-like cells can be developed using techniques routinely practiced by those of ordinary skill in the art. Thus, cultured spore-like cells and cell lines derived from spore-like cells can also be used to treat human patients.

Spore-like cells can differentiate into many different cell types. For example, as shown below, spore-like cells can be isolated from adult mammalian liver, lung, heart, bladder, kidney, and intestine, and can differentiate into hepatocytes, alveolar cells, cardiac myocytes, bladder cells, renal cells, and autonomic neurons, respectively. Spore-like cells can also be isolated from readily obtainable bodily fluids, such as the blood. Given the variety of known sources for spore-like cells, it is reasonable to expect that these cells can be found in most, if not all, tissues and bodily fluids. Similarly, given the number of differentiated phenotypes already observed, it is reasonable to expect that spore-like cells can differentiate into most, if not all, types of cells.

Spore-like cells were so-named because of their primitive appearance and tolerance for oxygen deprivation. Spore-like cells are typically small. Many cells in a culture of newly isolated spore-like cells are approximately 1 to 3µ in diameter. However, larger and smaller spore-like cells have been identified (e.g., using electron microscopy; see Example 2). Given that spore-like cells can differentiate into a variety of mature cell types, and that differentiation is a gradual process, it is difficult to define the precise upper size limit of spore-like cells. However, spore-like cells 4 to 5, and 7 to 10µ in diameter have been identified in scanning electron micrographs. Occasionally, even larger cells (e.g., cells as large as 12 to 18µ) may have been observed. The larger cells may be on the verge of cell division, or may be conglomerates of several spore-like cells. The lower size limit of the spore-like cells is more definite and is certainly unique. Spore-like cells that are only about one-third of a micron in diameter have been observed in scanning electron micrographs and some cells may be as small as one-tenth of a micron.

This extremely small size may reflect the unique composition of spore-like cells. As decribed below, newly isolated spore-like cells are generally spherical and contain a great deal of nuclear material and relatively little cytoplasm. In most differentiated cells, the nucleus consumes approximately 10-20% of the cells' volume. However, approximately 50% and up to approximately 90% of the volume of a spore-like cell is consumed with nuclear material. The nuclear material appears to be surrounded by a coat containing glycolipids and mucopolysaccharides. Without limiting the invention to spore-like cells that arise by any particular mechanism, it is believed that spore-like cells may arise when essential DNA fragments (which may represent compressed DNA) are shed from mature cells (e.g., those undergoing cell death by apoptosis or other means) and re-packaged in a glycolipid-rich coat. The unique size of newly-isolated spore-like cell is perhaps best appreciated by viewing the cells with an electron microscope (e.g., see FIGS. 1A-1C and 2A-2D).

Functionally, spore-like cells are unique in at least three ways. First, even though isolated from a mature (e.g., a post-natal, adolescent, or adult) animal, they can differentiate into a wide variety of different cell types. Second, spore-like cells have an exceptionally high tolerance for oxygen deprivation. Experiments have demonstrated that spore-like cells can tolerate essentially complete oxygen deprivation for at least 24 hours (cells were viable despite oxygen deprivation for either four or 24 hours). Thus, spore-like cells can tolerate prolonged oxygen deprivation for at least 24 hours and probably even longer. In addition, spore-like cells have a greater capacity to proliferate than terminally differentiated cells isolated from specialized tissues. Proliferative capacity is an important attribute because tissue engineering, cell therapies, and gene-based therapies are often hampered by physicians' inability to obtain sufficient numbers of cells to administer to a patient.

To obtain spore-like cells, a sample is obtained from an animal such as a human. One of the easiest samples to obtain is a sample of whole blood. Those of ordinary skill in the art will appreciate that the isolation method may vary slightly depending on the type of tissue used as the starting material. For example, in the event the sample is a blood sample, it can be placed in a tube containing an anti-coagulant. After collection, tissue samples, whether they are samples of bodily fluids or cell suspensions obtained from solid organs, are centrifuged for a time and at a speed sufficient to pellet the cells within the sample at the bottom of the centrifuge tube. The resulting pellet is resuspended in a suitable medium (e.g., DMEM/F-12 medium supplemented with glucose, transferrin, insulin, putricine, selenium, progesterone, epidermal growth factor (EGF) and basic fibroblast growth factor (bFGF; see the Examples, below).

The suspended cells are then transferred to a tissue culture vessel and incubated at or near 37° C. Initially, when the sample is a blood sample, the culture flasks contain primarily hematopoietic cells. However, after several days in culture, the red blood cells lyse and degenerate so that the culture contains primarily, if not exclusively, spore-like cells. When spore-like cells are isolated from solid tissues, the differentiated cells can be lysed by triturating the sample with a series of pipettes, each having a smaller bore diameter than the one before. For example, the last pipette used can have a bore diameter of approximately 15µ. After several additional days in culture, the spore-like cells multiply and can coalesce to form clusters of cells. Over time, usually on the order of approximately 7 days, their number can increase greatly. Typically, more than 90% of the cells are viable according to Trypan blue exclusion studies when isolated as described above.

Those of ordinary skill in the art will recognize that trituration through reduced bore pipettes is not the only way to isolate spore-like cells from larger, differentiated cells. For example, a suspension containing spore-like cells and differentiated cells can be passed through a filter having pores of a particular size. The size of the pores within the filter (and, similarly, the diameter of the pipette used for trituration) can be varied, depending on how stringent one wishes the isolation procedure to be. Generally, the smaller the pores within the filter, or the smaller the diameter of the pipette used for trituration, the fewer the number of differentiated cells that will survive the isolation procedure.

At the time of isolation, spore-like cells may not express any known markers (i.e., proteins or other biological molecules associated with a given terminally differentiated cell type). When placed in culture, some spore-like cells express nestin, a marker of neuroectodermally-derived cells. Those that do express nestin typically do so before they express markers associated with terminally differentiated cells. Spore-like cells or their progeny will eventually express cellular markers associated with terminally differentiated cells (see the Examples below). Those of ordinary skill in the art can identify, by techniques routinely practiced in the art (e.g., immunochemistry), numerous markers associated with terminally differentiated cells. Those of ordinary skill in the art can also readily compare the cytoarchitecture of spore-like cells, their precursors, and known terminally differentiated cells in order to distinguish one from another. This comparison can be made, for example, using electron microscopy.

The features and characteristics described above can be used to distinguish spore-like cells from previously identified cell types. For example, the spore-like cells of the invention can be identified by their ability to differentiate into a variety of terminally differentiated cell types found in mature animals (such as those illustrated in the Examples below), their typical spherical shape, small size (as small as 0.1-0.3μ in diameter and generally 1.0 to 3.0μ in diameter), and cytoarchitecture (which includes relatively large amounts of nuclear material, relatively small amounts of cytoplasm, and a glycolipid-rich coat), and their ability to survive in environments having a low or even non-existent oxygen supply.

When cultured as described in the Examples below, spore-like cells proliferate more rapidly and into more types of differentiated cells than do terminally differentiated cells or mesenchymal stem cells. Cell viability can be assessed using standard techniques, including visual observation with light or scanning electron microscopes and Trypan blue exclusion.

Spore-like cells have been isolated from body fluids (e.g., the blood) as well as from solid functional organs such as the liver, but it is not clear that they originate exclusively in either of these places. It may be that tissues and organs are the primary sources for spore-like cells, which appear in body fluids only secondarily, for example, when the cells are "washed out" of those tissues. However, it is also possible that spore-like cells originate in bodily fluids or from the same source as other cells that are present in bodily fluids (e.g., spore-like cells may originate in the bone marrow). If so, spore-like cells could then be subsequently delivered from those fluids to specific tissues. Moreover, delivery may be upregulated when the tissue is affected by, for example, a disorder, a regenerative process, or wound healing.

Without limiting the invention to spore-like cells that differentiate by a particular mechanism, it is believed that the rate and nature of spore-like cell differentiation can be influenced by altering the number and type of mature cells to which the spore-like cells are exposed. For example, when isolating spore-like cells from the liver, the more mature hepatocytes that remain in the culture of spore-like cells, the more quickly the spore-like cells will differentiate and the more likely it is that they will differentiate into hepatocytes. Thus, it is believed that spore-like cells proliferate and differentiate in response to agents (e.g., growth factors or hormones) within tissue, including tissue that has been injured or that is otherwise associated with a medical disorder. These agents guide differentiation so that the spore-like cells or their progeny come to express some or all of the same phenotypic markers expressed by mature cells normally present in the tissue in which they have been placed. Spore-like cells can be influenced by agents within tissues regardless of their origin (i.e., regardless of whether the spore-like cells originate in the blood, another body fluid, the bone marrow, or a solid, functional tissue or organ).

Spore-like cells can be used to maintain the integrity and function of a wide variety of tissues as well as to reengineer, repair, or otherwise improve tissue associated with a medical disorder. For example, spore-like cells can be used to maintain or reengineer: bone; bone marrow; muscle (e.g., smooth, skeletal, or cardiac muscle); connective tissue (e.g., cartilage, ligaments, tendons, pleura, or fibrous tissues); lung tissue; vascular tissue; nervous tissue (e.g., neurons and glial cells in the central or peripheral nervous systems), glandular tissue (e.g., tissue of the thyroid gland, adrenal gland, or sweat or sebaceous glands); epithelial cells, keratinocytes, or other components of the skin; lymph nodes; the immune system; reproductive organs; or any of the internal organs (e.g., liver, kidney, pancreas, stomach, bladder, or any portion of the alimentary canal). This list is intended to illustrate, not limit, the types of cells and tissues that can benefit from administration of spore-like cells. For example, lifelike artificial skin can be produced by culturing spore-like cells and allowing them, when applied to a living body or used in conjunction with present skin replacement methods, to differentiate into epidermal and dermal cells (including melanocytes) as well as into hair follicles, sweat glands, sebaceous glands, ganglia, and similar adnexal structures. Those of ordinary skill in the art will recognize many other therapeutic uses for spore-like cells.

Spore-like Cell Differentiation

Spore-like cells or their progeny can differentiate into a number of different cell types. For example, spore-like cells can differentiate into epithelial cells, keratinocytes, melanocytes, adipocytes, myocytes, chondrocytes, osteocytes, alveolar cells, hepatocytes, renal cells, adrenal cells, endothelial cells, islet cells (e.g., alpha cells, delta cells, PP cells, and beta cells), blood cells (e.g., leukocytes, erythrocytes, macrophages, and lymphocytes) retinal cells (and other cells involved in sensory perception, such as those that form hair cells in the ear or taste buds on the tongue), and fibroblasts or other cell types present in organs and connective tissues.

Spore-like cells and their progeny can be induced to differentiate in a variety of ways and may or may not be committed to a particular differentiation pathway. One method of inducing differentiation is to allow spore-like cells or their progeny to establish contact (e.g., physical contact) with a solid support. For example, spore-like cells can differentiate when they establish contact with (e.g., adhere to) a glass or plastic surface, a mesh, or other substrate suitable for use in tissue culture or administration to a patient.

Spore-like cells can also differentiate when they establish contact with a tissue within a patient's body or are sufficiently close to a tissue to be influenced by substances (e.g., growth factors, enzymes, or hormones) released from the tissue. Thus, differentiation of a spore-like cell can be influenced by virtue of signals the cell receives from the surrounding tissue. Such signalling would occur, for example, when a receptor on the surface of a spore-like cell, or on the surface of a cell descended from a spore-like cell, bound and transduced a signal from a molecule such as a growth factor, enzyme, or hormone that was released by a tissue within the patient.

Alternatively, or in addition, spore-like cells can be induced to differentiate by adding a substance (e.g., a growth factor, enzyme, hormone, or other signalling molecule) to the cell's environment. For example, a substance can be added to a culture dish containing spore-like cells, to a mesh or other substrate suitable for applying spore-like cells to a tissue, or to a tissue within a patient's body. When a substance that induces spore-like cells to differentiate is administered, either systemically or locally, it can be administered according to pharmaceutically accepted methods. For example, proteins, polypeptides, or oligonucleotides can be administered in a physiologically compatible buffer, with or without a carrier or excipient. Of course, either the cells within a patient's body or the cells being administered (here, spore-like cells or their progeny) can be made to express particular factors following genetic manipulation. For example, spore-like cells can be made to express hormones, such as insulin, by transfecting them with gene constructs that include sequences that encode these factors. Thus, spore-like cells or their progeny can differentiate either in culture or in a patient's body, and may do so following contact with a solid support or exposure to substances that are either naturally expressed, exogenously administered, or expressed as a result of genetic manipulation. Regardless of the stimulus for differentiation, spore-like cells that have differentiated, or that will do so, sufficiently to aid in the maintenance or repair of tissue, can be administered to a patient (e.g., at the site of a burn or other traumatized area of skin, a bone fracture, a torn ligament, an atrophied muscle, a malfunctioning gland, or an area adversely affected by a neurodegenerative process or autoimmune response).

Another way to promote proliferation without differentiation is to expose the spore-like cells, particularly those isolated from the skin, to agonists of Notch function, as described in U.S. Pat. No. 5,780,300. Agonists of Notch include, but are not limited to, proteins such as Delta or Serrate or Jagged (Lindsell et al., Cell 80:909-917, 1995) or biologically active fragments thereof. These proteins or protein fragments mediate binding to Notch and thereby activate the Notch pathway. Spore-like cells isolated from the skin can be contacted in culture with agonists of Notch or can be transfected with genes that encode Notch agonists. As described above, the techniques required to transfect cells in culture are routinely practiced by those of ordinary skill in the art. Spore-like cells that remain undifferentiated in culture can differentiate when administered to a patient; their differentiation being orchestrated by the microenvironment they encounter within the patient.

Figure 7A:
FIGS. 7A-7E are photographs of cells isolated from the liver of an adult rat. The newly isolated cells shown in FIGS. 7A and 7C include undifferentiated spore-like cells (magnification at 100×). After three days in culture, an aggregate of cells resembling a differentiating liver structure can be seen (FIG. 7B; magnification at 200×). After seven days in culture, cells resembling hepatocytes can be seen (FIG. 7D). After 12 days in culture, many cells isolated from the liver express bile, as evidenced by a Hall's stain (FIG. 7E; 400×).
Figure 7B:
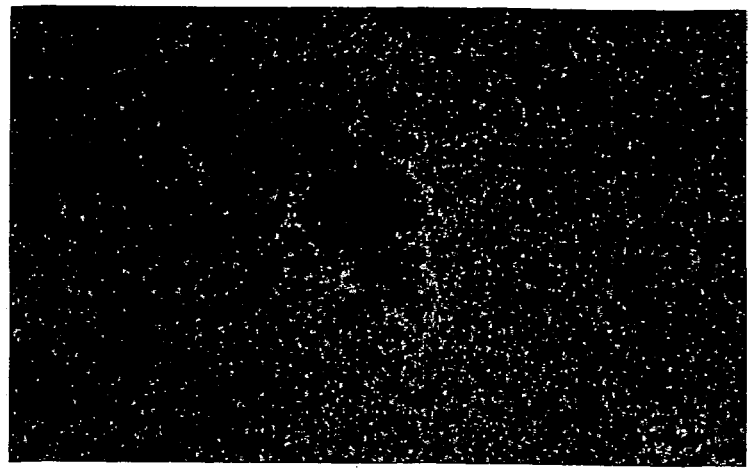
Figure 7C:
Figure 7D:
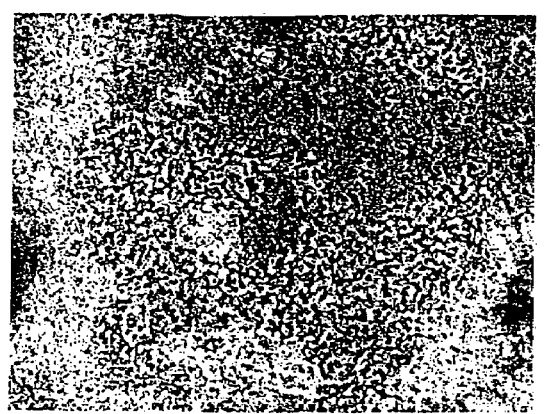
Figure 7E:
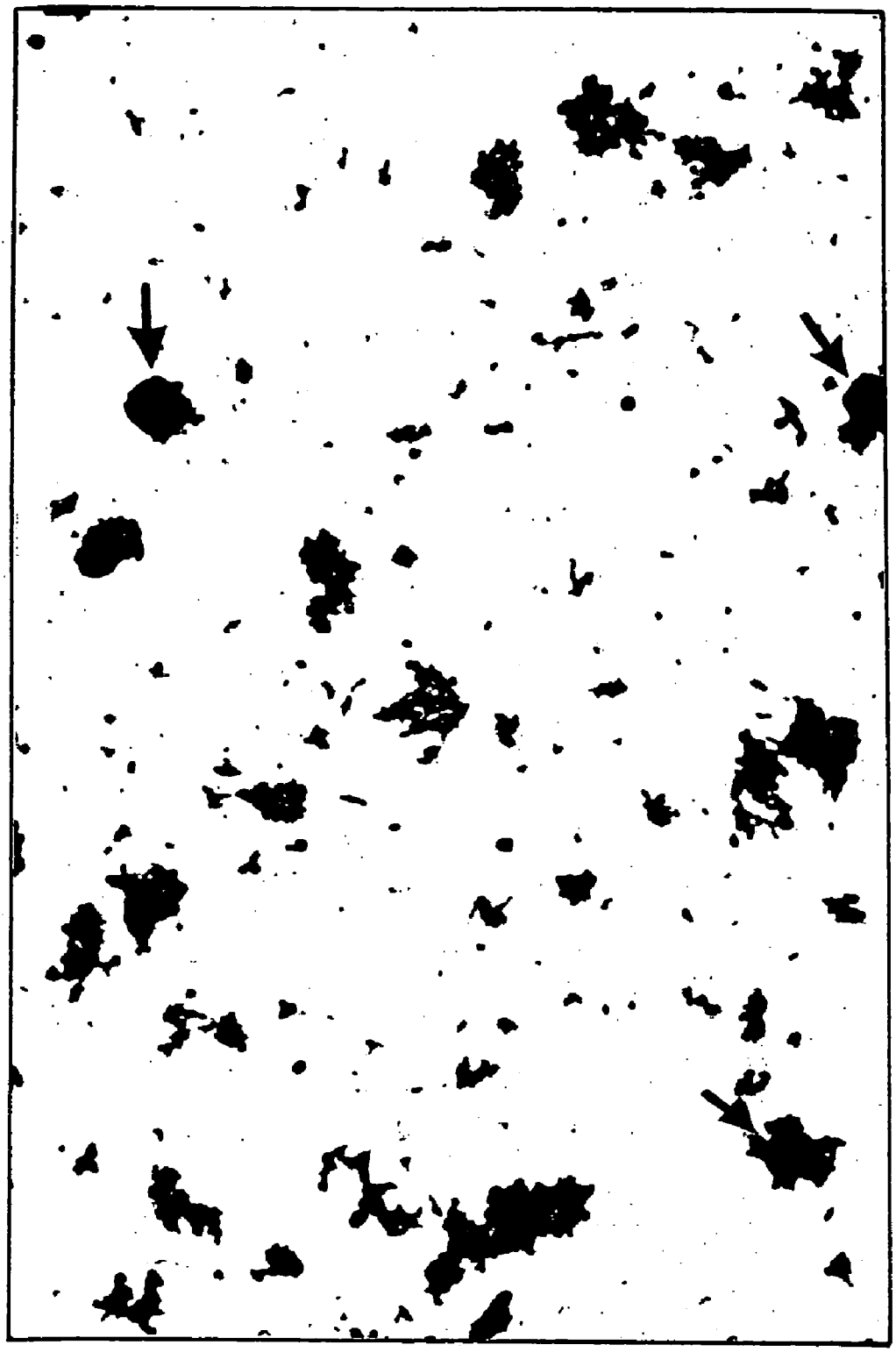

As described in Example 7, below, many cells isolated as spore-like cells from the liver express bile after 12 days in culture. Bile expression can be seen following staining by Hall's technique using Fouchet's reagent (FIG. 7E). Bile pigments can also be identified by at least two other standard histological stains, the Gmelin test, and Stein's method. Similarly, there are a number of standard assays for glycolipids, which are carbohydrate and lipid compounds that contain 1 mole each of a fatty acid, sphingosine, and hexose. Common reactions for carbohydrates include the periodic acid-Schiff (PAS) reaction, diastase, alcian blue staining, colloidal iron, and hyaluronidase. Spore-like cells isolated from adult liver are stained by PAS and mucicarmine stains, which indicates that these cells are coated with mucopolysaccharids and glycolipids.

While spore-like cells or their progeny may eventually become fully differentiated, and while this is desirable in some circumstances (e.g., where the cells are used to essentially recreate a histologically mature and complete tissue), fully differentiated cells are not always necessary for successful treatment; spore-like cells or their progeny need only differentiate to a point sufficient to treat the patient. For example, spore-like cells used to treat diabetes need not ever differentiate into cells that are indistinguishable from fully differentiated β cells within the islets of Langerhans. To the contrary, spore-like cells or their progeny need only differentiate to the point where they express sufficient insulin to treat the diabetic patient.

Excluded from the invention are cells having characteristics that render them indistinguishable from previously identified stem cells (e.g., mesenchymal stem cells), precursor cells (e.g., the islet cell precursors described by Cornelius et al. (*Horm. Metab. Res.* 29:271-277 (1997)), or the progenitors from central nervous tissue described by Shihabuddin et al. (*Exp. Neurol.* 148:577-586 (1997)) or Weiss et al. (*J. Neurosci.* 16:7599-7609 (1996)) or terminally differentiated cells. These characteristics can be assessed by those of ordinary skill in the art in numerous ways (e.g., by histological, biochemical, or, preferably, electron microscopic analysis).

Methods of Treatment

A. Administration of Spore-like Cells and their Progeny via Hydrogel

The novel cell types described herein can be administered to a patient by way of a composition that includes spore-like cells, or their progeny, and a liquid hydrogel. This cell-hydrogel mixture can be applied directly to a tissue that has been damaged. For example, as described in U.S. Ser. No. 08/747,036, a hydrogel-cell mixture can simply be brushed, dripped, or sprayed onto a desired surface or poured or otherwise made to fill a desired cavity or device. The hydrogel provides a thin matrix or scaffold within which the spore-like cells adhere and grow. These methods of administration may be especially well suited when the tissue associated with a patient's disorder has an irregular shape or when the cells are applied at a distant site (e.g., when spore-like cells are placed beneath the renal capsule to treat diabetes).

Alternatively, the hydrogel-cell mixture can be introduced into a permeable, biocompatible support structure so that the mixture essentially fills the support structure and, as it solidifies, assumes the support structure's shape. Thus, the support structure can guide the development and shape of the tissue that matures from spore-like cells, or their progeny, that are placed within it. As described further below, the support structure can be provided to a patient either before or after being filled with the hydrogel-cell mixture. For example, the support structure can be placed within a tissue (e.g., a damaged area of the skin, the liver, or the skeletal system) and subsequently filled with the hydrogel-cell composition using a syringe, catheter, or other suitable device. When desirable, the shape of the support structure can be made to conform to the shape of the damaged tissue. In the following subsections, suitable support structures, hydrogels, and delivery methods are described (cells suitable for use are described above).

1. Hydrogels

The hydrogels used to practice this invention should be biocompatible, biodegradable, capable of sustaining living cells, and, preferably, capable of solidifying rapidly in vivo (e.g., in about five minutes after being delivered to the support structure). Large numbers of spore-like cells can be distributed evenly within a hydrogel; a hydrogel can support approximately $5 \times 10^6$ cells/ml. Hydrogels also enable diffusion so that nutrients reach the cells and waste products can be carried away.

A variety of different hydrogels can be used to practice the invention. These include, but are not limited to: (1) temperature dependent hydrogels that solidify or set at body temperature (e.g., PLURONICS™); (2) hydrogels cross-linked by ions (e.g., sodium alginate); (3) hydrogels set by exposure to either visible or ultraviolet light, (e.g., polyethylene glycol polylactic acid copolymers with acrylate end groups); and (4) hydrogels that are set or solidified upon a change in pH (e.g., TETRONICS™).

Materials that can be used to form these different hydrogels include, but are not limited to, polysaccharides such as alginate, polyphosphazenes, and polyacrylates, which are cross-linked ionically, block copolymers such as PLURONICS™ (also known as POLOXAMERS™), which are poly(oxyethylene)-poly(oxypropylene) block polymers solidified by changes in temperature, TETRONICS™ (also known as POLOXAMINES™), which are poly(oxyethylene)-poly(oxypropylene) block polymers of ethylene diamine solidified by changes in pH.

Ionic Hydrogels

Ionic polysaccharides, such as alginates or chitosan, can also be used to suspend living cells, including spore-like cells and their progeny. These hydrogels can be produced by cross-linking the anionic salt of alginic acid, a carbohydrate polymer isolated from seaweed, with ions, such as calcium cations. The strength of the hydrogel increases with either increasing concentrations of calcium ions or alginate. U.S. Pat. No. 4,352,883 describes the ionic cross-linking of alginate with divalent cations, in water, at room temperature, to form a hydrogel matrix.

Spore-like cells are mixed with an alginate solution, the solution is delivered to an already implanted support structure, which then solidifies in a short time due to the presence of physiological concentrations of calcium ions in vivo. Alternatively, the solution is delivered to the support structure prior to implantation and solidified in an external solution containing calcium ions.

In general, these polymers are at least partially soluble in aqueous solutions (e.g., water, aqueous alcohol solutions that have charged side groups, or monovalent ionic salts thereof). There are many examples of polymers with acidic side groups that can be reacted with cations (e.g., poly(phosphazenes), poly(acrylic acids), and poly(methacrylic acids)). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two different types of side chains: acidic side chains capable of forming salt bridges with multivalent cations, and side chains that hydrolyze in vivo (e.g., imidazole groups, amino acid esters, glycerol, and glucosyl). Bioerodible or biodegradable polymers (i.e., polymers that dissolve or degrade within a period that is acceptable in the desired application (usually in vivo therapy), will degrade in less than about five years and most preferably in less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described above are known to those of ordinary skill in the art. See, for example *Concise Encyclopedia of Polymer Science and Engineering*, J. I. Kroschwitz, Ed., John Wiley and Sons, New York, N.Y., 1990. Many polymers, such as poly(acrylic acid), alginates, and PLURONICS™ are commercially available.

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 10 and 18.5 kDa. Smaller polymers result in gels of higher density with smaller pores.

Temperature-Dependent Hydrogels

Temperature-dependent, or thermosensitive, hydrogels can also be used in the methods of the invention. These hydrogels have so-called "reverse gelation" properties, i.e., they are liquids at or below room temperature, and gel when warmed to higher temperatures (e.g., body temperature). Thus, these hydrogels can be easily applied at or below room temperature as a liquid and automatically form a semi-solid gel when warmed to body temperature. As a result, these gels are especially useful when the support structure is first implanted into a patient, and then filled with the hydrogel-cell composition. Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers.

These copolymers can be manipulated by standard techniques to affect their physical properties such as porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration. These gels have diffusion characteristics capable of allowing spore-like cells and their progeny to survive and be nourished.

U.S. Pat. No. 4,188,373 describes using PLURONIC™ polyols in aqueous compositions to provide thermal gelling aqueous systems. U.S. Pat. Nos. 4,474,751, '752, '753, and 4,478,822 describe drug delivery systems that utilize thermosetting polyoxyalkylene gels. With these systems, both the gel transition temperature and/or the rigidity of the gel can be modified by adjustment of the pH and/or the ionic strength, as well as by the concentration of the polymer.

pH-Dependent Hydrogels

Other hydrogels suitable for use in the methods of the invention are pH-dependent. These hydrogels are liquids at, below, or above specific pH values, and gel when exposed to specific pHs, for example, 7.35 to 7.45, the normal pH range of extracellular fluids within the human body. Thus, these hydrogels can be easily delivered to an implanted support structure as a liquid and automatically form a semi-solid gel when exposed to body pH. Examples of such pH-dependent hydrogels are TETRONICS™ (BASF-Wyandotte) polyoxyethylene-polyoxypropylene polymers of ethylene diamine, poly(diethyl aminoethyl methacrylate-g-ethylene glycol), and poly(2-hydroxymethyl methacrylate). These copolymers can be manipulated by standard techniques to affect their physical properties.

Light Solidified Hydrogels

Other hydrogels that can be used to administer spore-like cells or their progeny are solidified by either visible or ultraviolet light. These hydrogels are made of macromers including a water soluble region, a biodegradable region, and at least two polymerizable regions (see, e.g., U.S. Pat. No. 5,410, 016). For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, for example, long wavelength ultraviolet light.

Examples of such light solidified hydrogels include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

Thus, a variety of hydrogels can be used to practice the present invention. They include, but are not limited to: (1) temperature dependent hydrogels that solidify or set at body temperature, e.g., PLURONICS™; (2) hydrogels cross-linked by ions, e.g., sodium alginate; (3) hydrogels set by exposure to either visible or ultraviolet light, e.g., polyethylene glycol polylactic acid copolymers with acrylate end groups; and (4) hydrogels that are set or solidified upon a change in pH, e.g., TETRONICS™.

The materials that can be used to form these various hydrogels include polysaccharides such as alginate, polyphosphazenes, and polyacrylates, which are cross-linked ionically, or block copolymers such as PLURONICS™ (also known as POLOXAMERS™), which are poly(oxyethylene)poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

2. Preparation of Hydrogel-Cell Mixtures

Once a hydrogel of choice (e.g., a thermosensitive polymer at between 5 and 25% (W/V), or an ionic hydrogel such as alginate dissolved in an aqueous solution (e.g., a 0.1 M potassium phosphate solution, at physiological pH, to a concentration between 0.5% to 2% by weight) is prepared, isolated spore-like cells or their progeny are suspended in the polymer solution. If desired, the concentration of the cells can mimic that of the tissue to be generated. For example, the concentration of cells can range between 10 and 100 million cells/ml (e.g., between 20 and 50 million cells/ml or between 50 and 80 million cells/ml). Of course, the optimal concentration of cells to be delivered into the support structure may be determined on a case by case basis, and may vary depending on cell type and the region of the patient's body into which the support structure is implanted or onto which it is applied. To optimize the procedure (i.e., to provide optimal viscosity and cell number), one need only vary the concentrations of the cells or the hydrogel.

3. Support Structures

The support structure is a permeable structure having pore-like cavities or interstices that shape and support the hydrogel-cell mixture. For example, the support structure can be a porous polymer mesh, or a natural or synthetic sponge. The porosity of the support structure should be such that nutrients can diffuse into the structure, thereby effectively reaching the cells inside, and waste products produced by the cells can diffuse out of the structure.

The support structure can be shaped to conform to the space in which new tissue is desired. For example, the support structure can be shaped to conform to the shape of an area of the skin that has been burned or the portion of cartilage or bone that has been lost. Depending on the material from which it is made, the support structure can be shaped by cutting, molding, casting, or any other method that produces a desired shape (as described below, in some instances, the support structure can be shaped by hand). Moreover, the shaping process can occur either before or after the support structure is filled with the hydrogel-cell mixture. For example, a support structure can be filled with a hydrogel-cell mixture and, as the hydrogel hardens, molded into a desired shape by hand.

As the hydrogel solidifies, it will adopt the flexibility and resiliency of the support structure, which is important for accommodation of compressive and tensile forces. Thus, for example, replaced skin could accommodate tensile forces associated with pulling and stretching, as well as compressive forces associated with weight bearing, as occurs, for example, on the soles of the feet. The flexibility and resiliency of the support structure also provides greater ease of administration. For example, in many currently available skin replacement methods, the tissue is extremely delicate and must be handled with the utmost care.

The support structure is also biocompatible (i.e., it is not toxic to the spore-like cells suspended therein) and can be biodegradable. Thus, the support structure can be formed from a synthetic polymer such as a polyanhydride, polyorthoester, or polyglycolic acid. The polymer should provide the support structure with an adequate shape and promote cell growth and proliferation by allowing nutrients to reach the cells by diffusion. Additional factors, such as growth factors, other factors that induce differentiation or dedifferentiation, secretion products, immunomodulators, anti-inflammatory agents, regression factors, biologically active compounds that promote innervation or enhance the lymphatic network, and drugs, can be incorporated into the polymer support structure.

An example of a suitable polymer is polyglactin, which is a 90:10 copolymer of glycolide and lactide, and is manufactured as VICRYL™ braided absorbable suture (Ethicon Co., Somerville, N.J.). Polymer fibers (such as VICRYL™), can be woven or compressed into a felt-like polymer sheet, which can then be cut into any desired shape.

Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid binds the crosslinks of the polyglycolic acid fibers, thereby coating these individual fibers and fixing the shape of the molded fibers. The polylactic acid also fills in the spaces between the fibers. Thus, porosity can be varied according to the amount of polylactic acid introduced into the support. The pressure required to mold the fiber mesh into a desirable shape can be quite moderate. All that is required is that the fibers are held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated from a mold having the relief pattern of the desired shape. Polymer gels can also be molded into thin, permeable polymer structures using compression molding techniques known in the art.

Many other types of support structures are also possible. For example, the support structure can be formed from sponges, foams, corals, or biocompatible inorganic structures having internal pores, or mesh sheets of interwoven polymer fibers. These support structures can be prepared using known methods.

4. Application of the Support Structure

Figure 13:
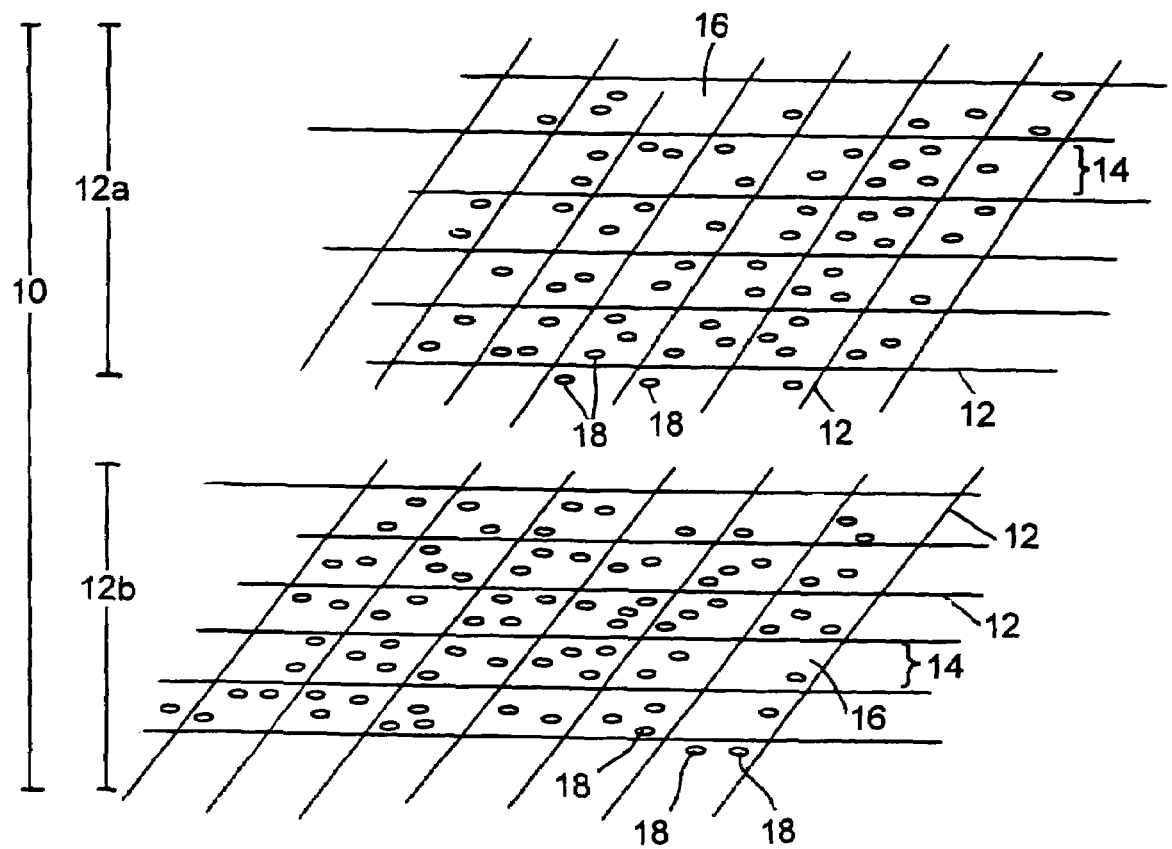
FIG. 13 is a schematic of a permeable support structure filled with a hydrogel-spore-like cell composition.

Any of the liquid hydrogel-cell mixtures described above can be placed in any of the permeable support structures (also described above). FIG. 13 is a schematic of a filled support structure in cross-section. This structure is suitable for application of spore-like cells or their progeny to the skin. The support structure 10 is formed from a bilayered mesh of interwoven polymer fibers 12 having epidermal layer 12a and dermal layer 12b. The spaces between the fibers form interconnected pores 14 that are filled with liquid hydrogel-cell mixture. Within a short time of placing the mixture in the support structure (e.g., in approximately three to five minutes), hydrogel 16 solidifies, thereby keeping the suspended cells 18 within the pores 14 of support structure 10. The solidified hydrogel 16 helps maintain the viability of the cells by allowing diffusion of nutrients (including growth and differentiation factors) and waste products through the interconnected pores of the support structure. The ultimate result being the growth of new skin and its engraftment to the patient's body.

The liquid hydrogel-cell mixture can be delivered to the shaped support structure either before or after the support structure is implanted in or applied to a patient. The specific method of delivery will depend on whether the support structure is sufficiently "sponge-like" for the given viscosity of the hydrogel-cell composition, i.e., whether the support structure easily retains the liquid hydrogel-cell mixture before it solidifies. Sponge-like support structures can be immersed within, and saturated with, the liquid hydrogel-cell mixture, and subsequently removed from the mixture. The hydrogel is then allowed to solidify within the support structure. The hydrogel-cell-containing support structure is then implanted in or otherwise administered to the patient.

The support structure can also be applied to the patient before the hydrogel completely solidifies. Alternatively, a sponge-like support structure can be injected with the liquid hydrogel-cell mixture, either before or after the support structure is implanted in or otherwise administered to the patient. The hydrogel-cell mixture is then allowed to solidify.

The volume of the liquid hydrogel-cell mixture injected into the support structure is typically less than, but somewhat comparable to, the volume of the support structure, i.e., the volume of the desired tissue to be grown.

Support structures that do not easily retain the liquid composition require somewhat different methods. In those cases, for example, the support structure is immersed within and saturated with the liquid hydrogel-cell mixture, which is then allowed to partially solidify. Once the cell-containing hydrogel has solidified to the point where the support structure can retain the hydrogel, the support structure is removed from the partially solidified hydrogel, and, if necessary, partially solidified hydrogel that remains attached to the outside of the support structure is removed (e.g., scraped off the structure).

Alternatively, the liquid hydrogel-cell mixture can be delivered into a mold containing the support structure. For example, the liquid hydrogel-cell mixture can be injected into an otherwise fluid-tight mold that contains the support structure and matches its outer shape and size. The hydrogel is then solidified within the mold, for example, by heating, cooling, light-exposure, or pH adjustment, after which, the hydrogel-cell-containing support structure can be removed from the mold in a form that is ready for administration to a patient.

In other embodiments, the support structure is implanted in or otherwise administered to the patient (e.g., placed over the site of a burn or other wound, placed beneath the renal capsule, or within a region of the body damaged by ischemia), and the liquid hydrogel-cell mixture is then delivered to the support structure. The hydrogel-cell mixture can be delivered to the support using any simple device, such as a syringe or catheter, or merely by pouring or brushing a liquid gel onto a support structure (e.g., a sheet-like structure).

Here again, the volume of hydrogel-cell composition added to the support structure should approximate the size of the support structure (i.e., the volume displaced by the desired tissue to be grown). The support structure provides space and a structural template for the injected liquid hydrogel-cell mixture. As described above, some of the hydrogel-cell mixture may leak from the support structure prior to solidifying. However, in this event, existing tissue beneath or surrounding the support structure would sufficiently constrain the liquid hydrogel-cell mixture until it gels.

In any of the above cases, the hydrogel is solidified using a method that corresponds to the particular hydrogel used (e.g., gently heating a composition including a PLURONIC™ temperature-sensitive hydrogel).

To apply or implant the support structure, the implantation site within the patient can be prepared (e.g., in the event the support structure is applied to the skin, the area can be prepared by debridement), and the support structure can be implanted or otherwise applied directly at that site. If necessary, during implantation, the site can be cleared of bodily fluids such as blood (e.g., with a burst of air or suction).

EXAMPLES

The present invention will be further understood by reference to the following non-limiting examples.

Example 1

Figure 11:
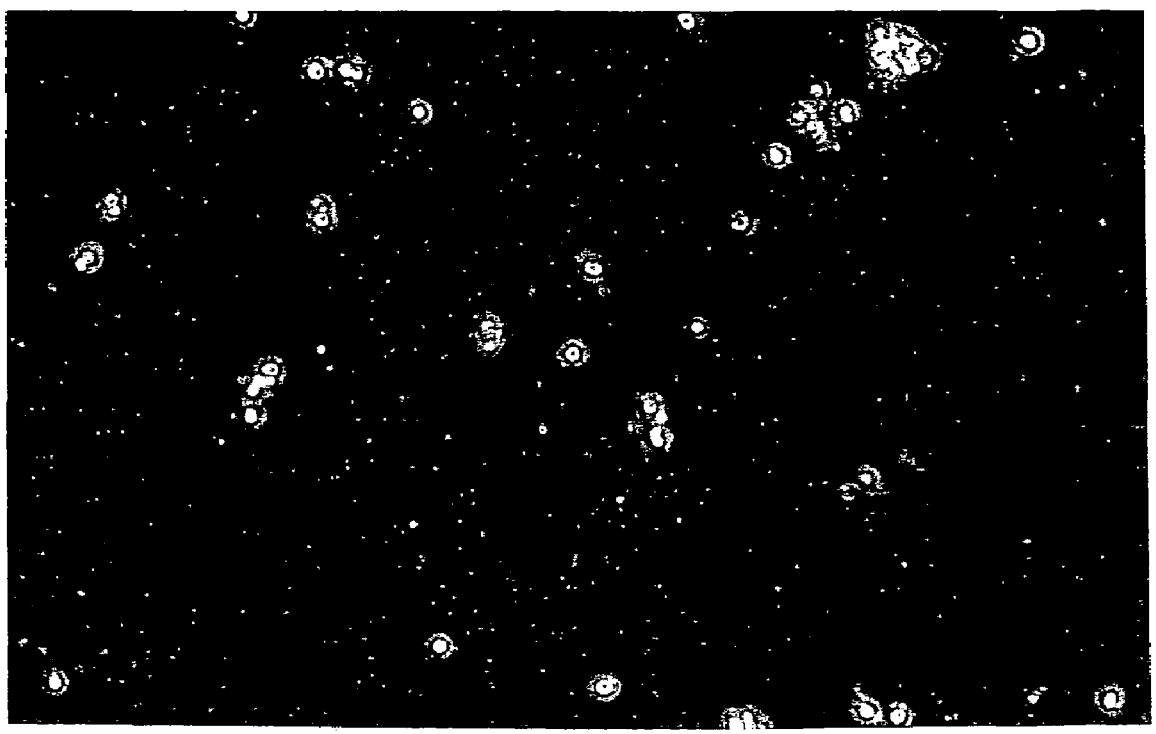
FIG. 11 is a photograph of a culture that includes undifferentiated spore-like cells isolated from adult human blood.
Figure 12A:
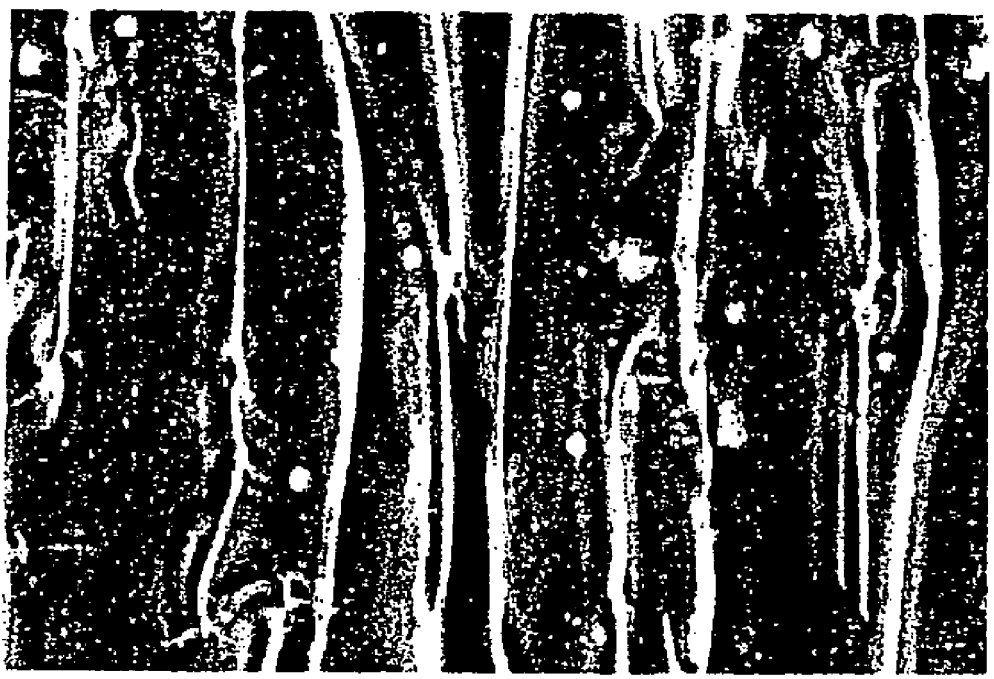
FIGS. 12A and 12B are photographs of cultured cells. The cultures were established seven days earlier and contained spore-like cells isolated from adult human blood.

Spore-like cells were isolated from human blood as follows. Five cc's of whole blood were acquired from an adult human and placed in a tube containing an anti-coagulant. The blood sample was then centrifuged at 1200 rpm for approximately five minutes. The supernatant was removed and the resulting pellet was resuspended in 15 cc's of DMEM/F-12 medium supplemented with a combination of the following hormones and nutrients: glucose (23 mM), transferrin (10 mg/ml), insulin (20 mg/ml), putricine (10 mM), selenium (100 nM), progesterone (10 nM) (Life Technologies, Baltimore, Md.), EGF (20 ng/ml), and bFGF (20 ng/ml) (Collaborative Biomedical Products, Chicago, Ill.). The resulting suspension was transferred to 75 $cm^2$ tissue culture flasks and incubated in 5% $CO_2$ at 37° C. The media were changed every 3-4 days. Cells were passaged every 7-9 days. Initially, these culture flasks appeared to contain many hematopoeitic cells (e.g., red blood cells), but over time (usually, a matter of several days), these cells disappeared, leaving only spore-like cells. After several days in culture, the spore-like cells multiplied and coalesced to form clusters of cells. Trypan blue exclusion revealed cell viability to be greater than 90%. FIGS. 11 and 12A are photographs of cultures that include undifferentiated spore-like cells isolated from adult human blood. The cells shown in FIG. 12A were isolated seven days earlier and are viewed with phase contrast microscopy.

Figure 12B:
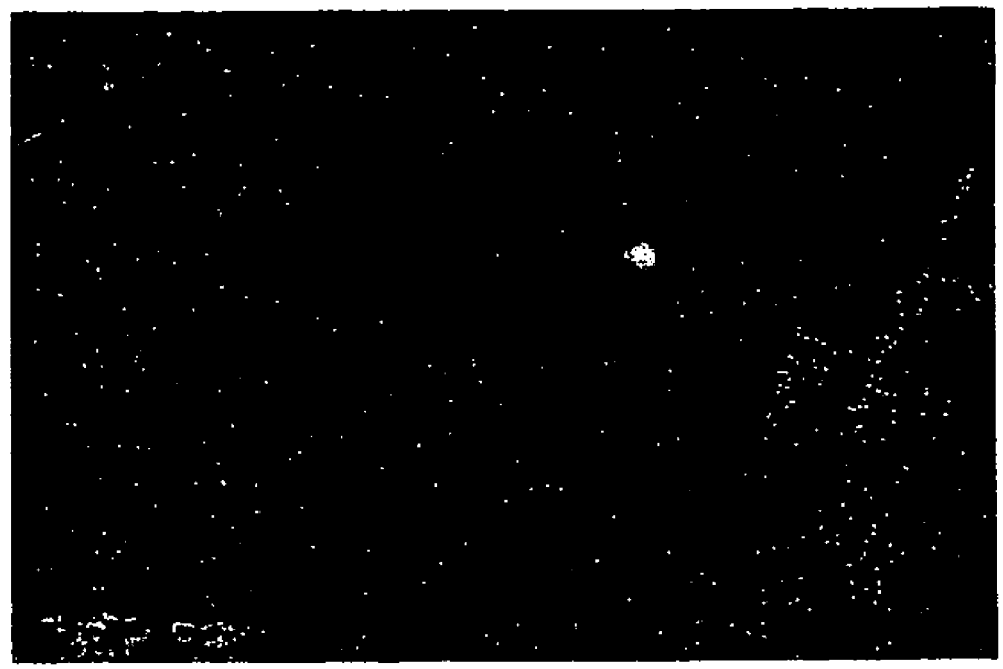

Immunofluorescent staining was then performed. At this time, some of the cells expressed nestin (see FIG. 12B).

Example 2

Spore-like cells were isolated from the skin of an adult rodent as follows. Excisional biopsies of the skin of adult Fisher rats were made under sterile conditions. The biopsied tissue, which included the dermis and epidermis, was placed in a petri dish containing cold (50° C.) phosphate buffered saline (PBS) and antibiotics (penicillin (50 mU/ml) and streptomycin (90 mg/ml)). The epidermis was scraped with a #11 scalpel to disassociate epidermal cells, and the tissue was then transferred to a second petri dish (also containing cold PBS and antibiotics) where the dermis was scraped with a #11 scalpel. The cells that were dissociated were then centrifuged at 1200 rpm (GLC-2B, Sorvall, Wilmington, Del.) for five minutes and resuspended in 10 ml of 0.05% trypsin (Life Technologies, Baltimore, Md.). Following resuspension in trypsin, the tissue was incubated at 37° C. for five minutes. Ten ml of Dulbecco's Modified Eagle Medium (DMEM)/F-12 containing 10% heat inactivated fetal bovine serum (FBS) (Life Technologies, Baltimore, Md.) was added to deactivate the trypsin.

The tissue was then triturated, first with a normal bore Pasteur pipette and subsequently with a series of fire polished pipettes having bores reduced to about 15 μm. The number of pipettes required can vary depending upon how frequently they become clogged with tissue. Trituration was carried out until the tissue was dispersed as a fine suspension. The suspension was then centrifuged at 1200 rpm (GLC-2B, Sorvall, Wilmington, Del.) for five minutes. The supernatant was removed and the pellet was resuspended in 15 ml of DMEM/F-12 medium supplemented with a hormone mixture containing glucose (23 mM), transferrin (10 mg/ml) insulin (20 mg/ml), putricine (10 mM), selenium (100 nM), progesterone (10 nM) (Life Technologies, Baltimore, Md.), EGF (20 ng/ml) and bFGF (20 ng/ml) (Collaborative Biomedical Products, Chicago, Ill.). The suspension was transferred to 75 $cm^2$ tissue culture flasks (Collaborative Biomedical Products, Chicago, Ill.) and incubated at 37° C. in 5% $CO_2$. The media was changed every three days and cells were passaged every 7-9 days. The cells that attached to the tissue culture flask appeared to differentiate more readily.

Spore-like cells isolated from the skin will differentiate upon exposure to the processes and basal nutrient media described in U.S. Pat. No. 5,292,655. Alternatively, growth factors that cause spore-like cells to mitose (e.g., epidermal growth factor (EGF), basic fibroblast growth factor (bFGF) and other cytokines) can be applied to help maintain the cells in an undifferentiated state. For example, the isolated cells can be cultured in Dulbecco's Modified Eagle's Medium (DMEM) supplemented with a hormone mixture containing glucose, transferrin, insulin, putricine, selenium, progesterone, EGF, and bFGF.

Spore-like cells were also isolated from excisional biopsies of the skin of adult pigs according to the same protocol described here for the adult rat.

Example 3

Figure 3A:
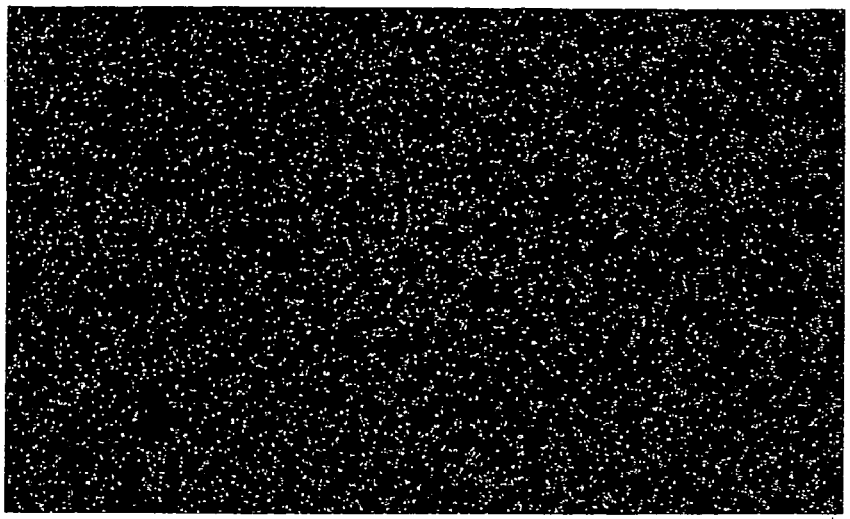
FIGS. 3A-3C are photographs of cells isolated from an adult rat heart and placed in culture. The newly isolated cells shown in FIG. 3A include undifferentiated spore-like cells (magnified 100×). After three days in culture, early myocardial cells can be seen (FIG. 3B). After two weeks in culture, Purkinje-like structures can be seen (FIG. 3C).
Figure 3B:
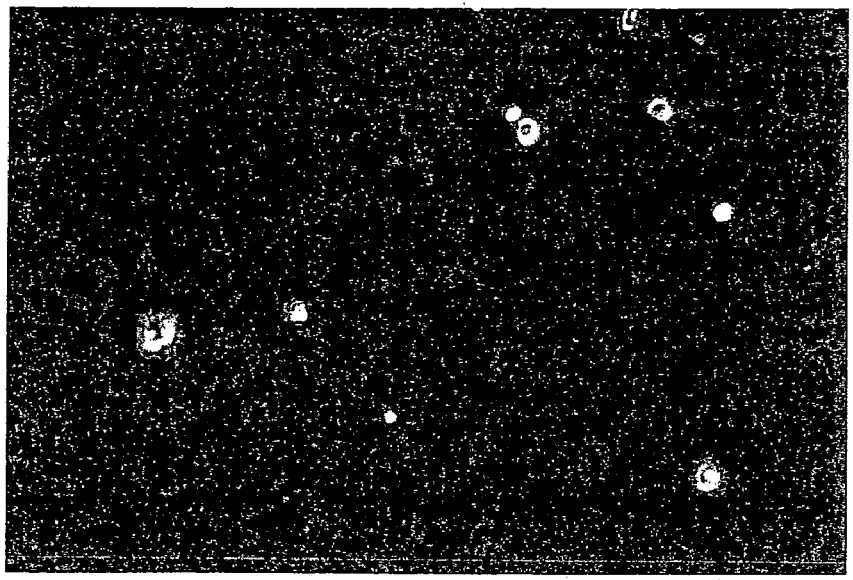
Figure 3C:
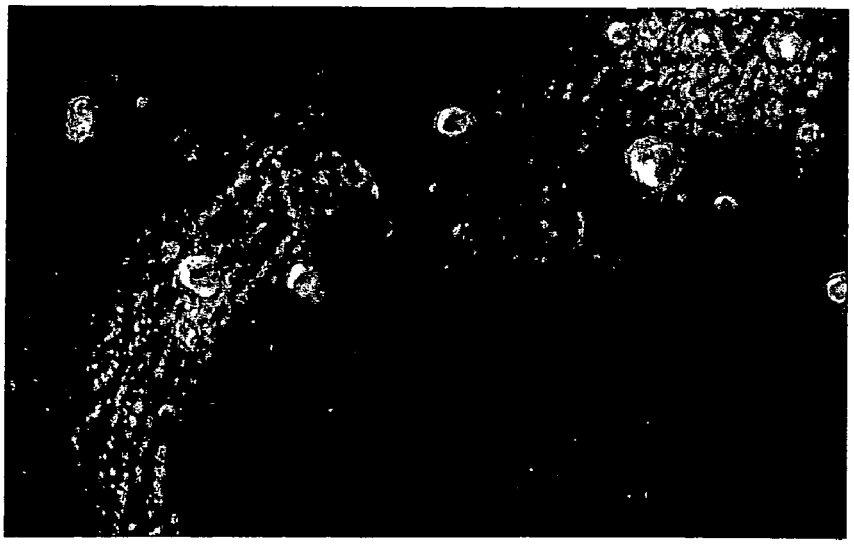

Spore-like cells were isolated from adult rat heart according to the protocol described in Example 2. The newly isolated cells, which are shown in FIG. 3A, include undifferentiated spore-like cells. After three days in culture, early myocardial cells can be seen (FIG. 3B), and after two weeks in culture, Purkinje-like structures can be seen (FIG. 3C).

Example 4

Figure 4A:
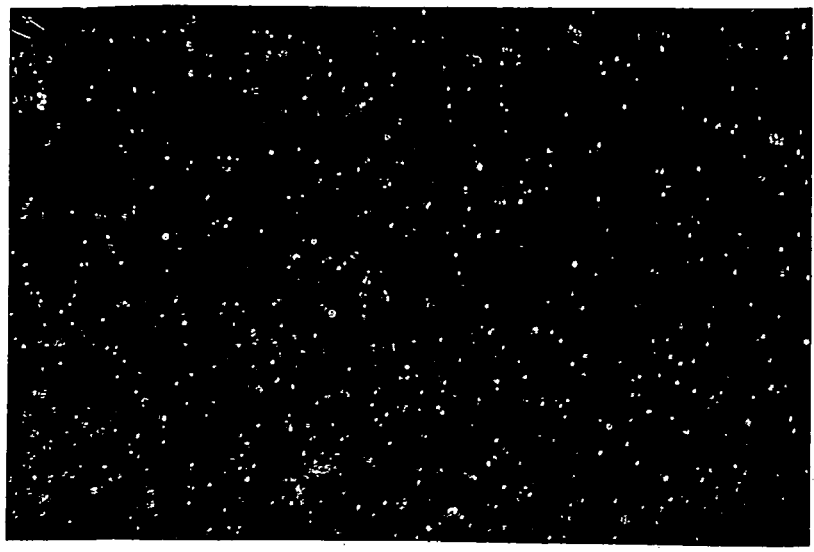
FIGS. 4A-4C are photographs of cells isolated from the small intestine of an adult rat. The newly isolated cells shown in FIG. 4A include undifferentiated spore-like cells. After three days in culture, clusters of small intestinal cells (FIG. 4B) and autonomic neurons (FIG. 4C) can be seen.
Figure 4B:
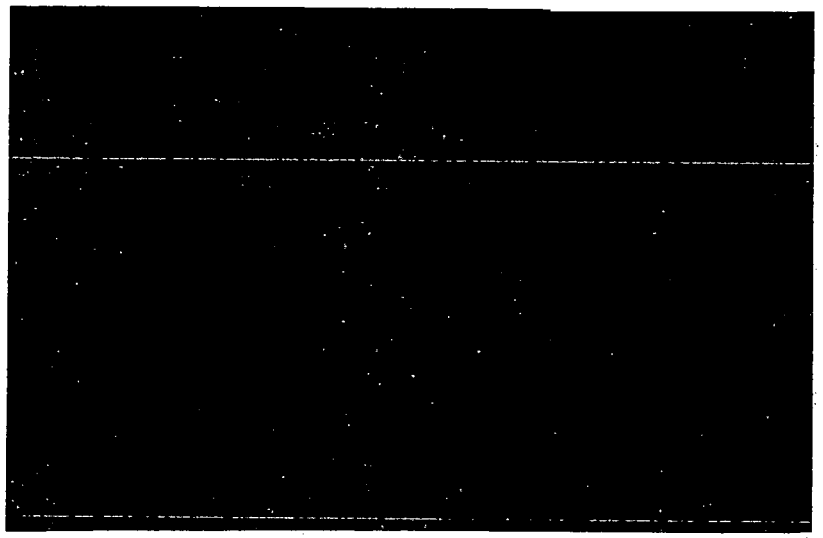
Figure 4C:
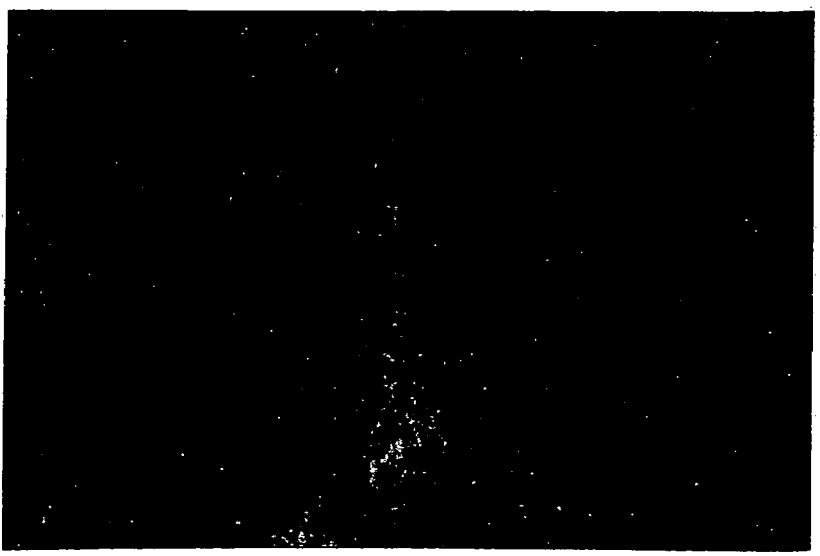

Spore-like cells were isolated from adult rat intestine according to the protocol described in Example 2. The newly isolated cells, as shown in FIG. 4A, include undifferentiated spore-like cells. After three days in culture, clusters of small intestinal cells (FIG. 4B) and autonomic neurons (FIG. 4C) can be seen.

Example 5

Figure 5A:
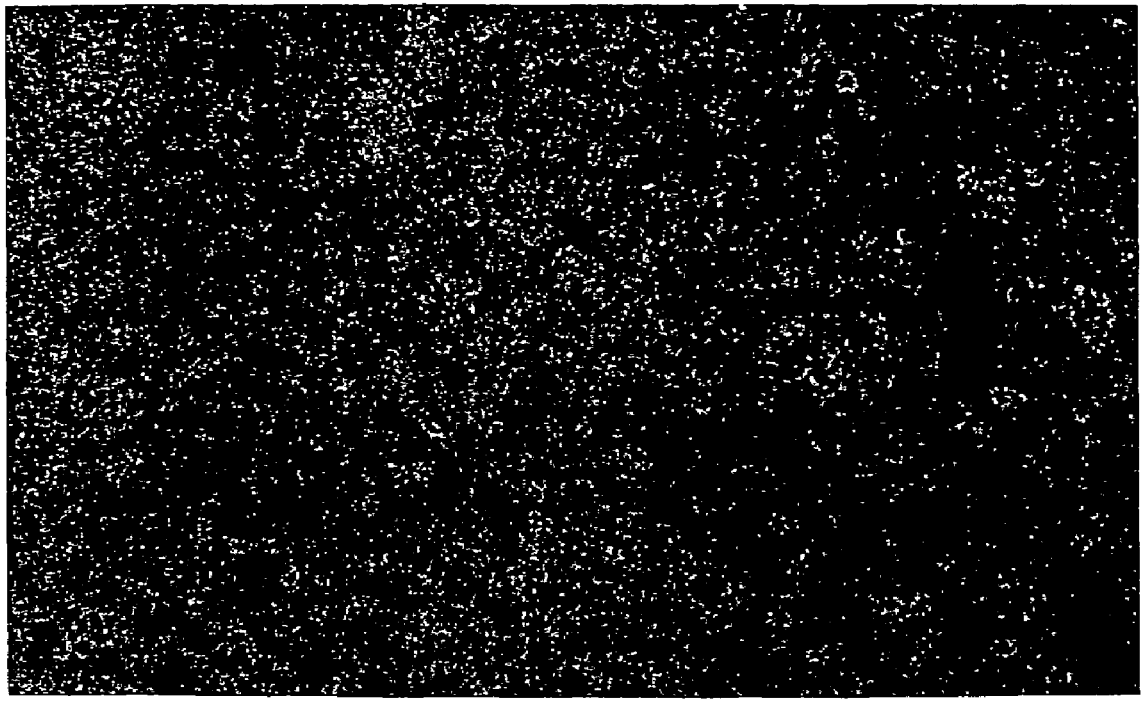
FIGS. 5A and 5B are photographs of cells isolated from the bladder of an adult rat. The newly isolated cells shown in FIG. 5A include undifferentiated spore-like cells (magnification at 100×). After two days in culture, the isolated spore-like cells, or their progeny, appear to be differentiating (FIG. 5B; magnification at 200×).
Figure 5B:
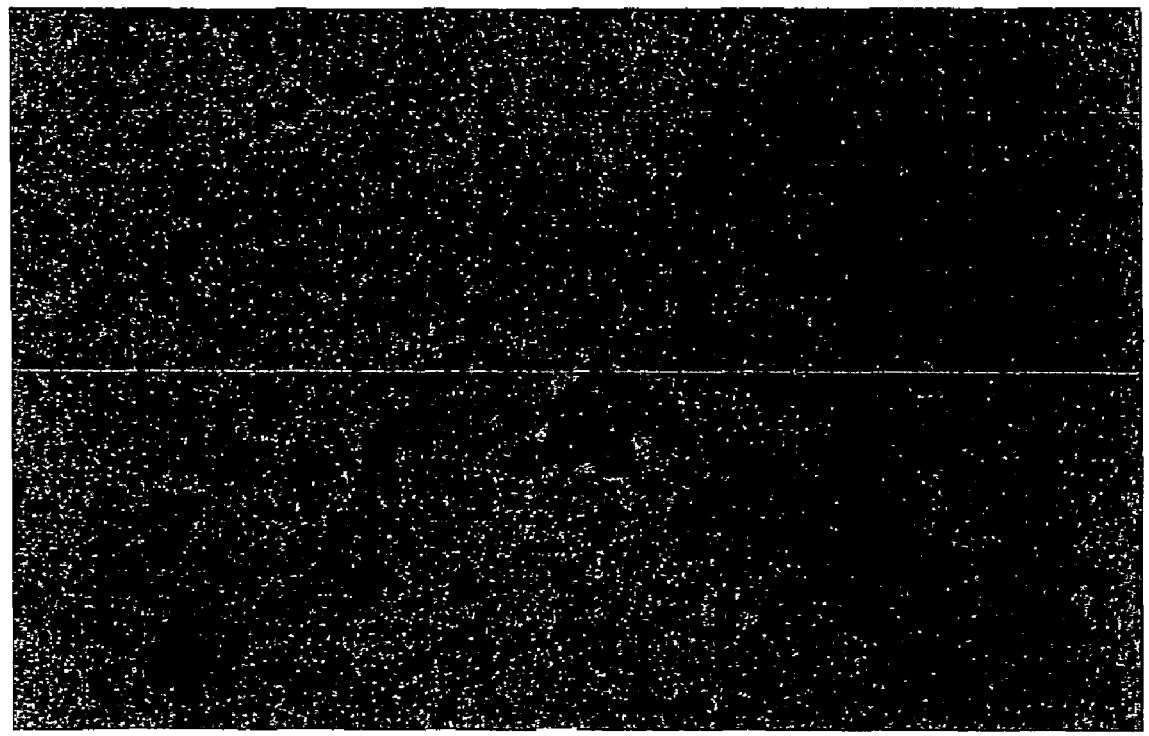

Spore-like cells were isolated from an adult rat bladder according to the protocol described in Example 2. The newly isolated cells, which are shown in FIG. 5A, include undifferentiated spore-like cells. After two days in culture, the isolated spore-like cells, or their progeny, appear to be differentiating into mature bladder cells (FIG. 5B).

Example 6

Figure 6A:
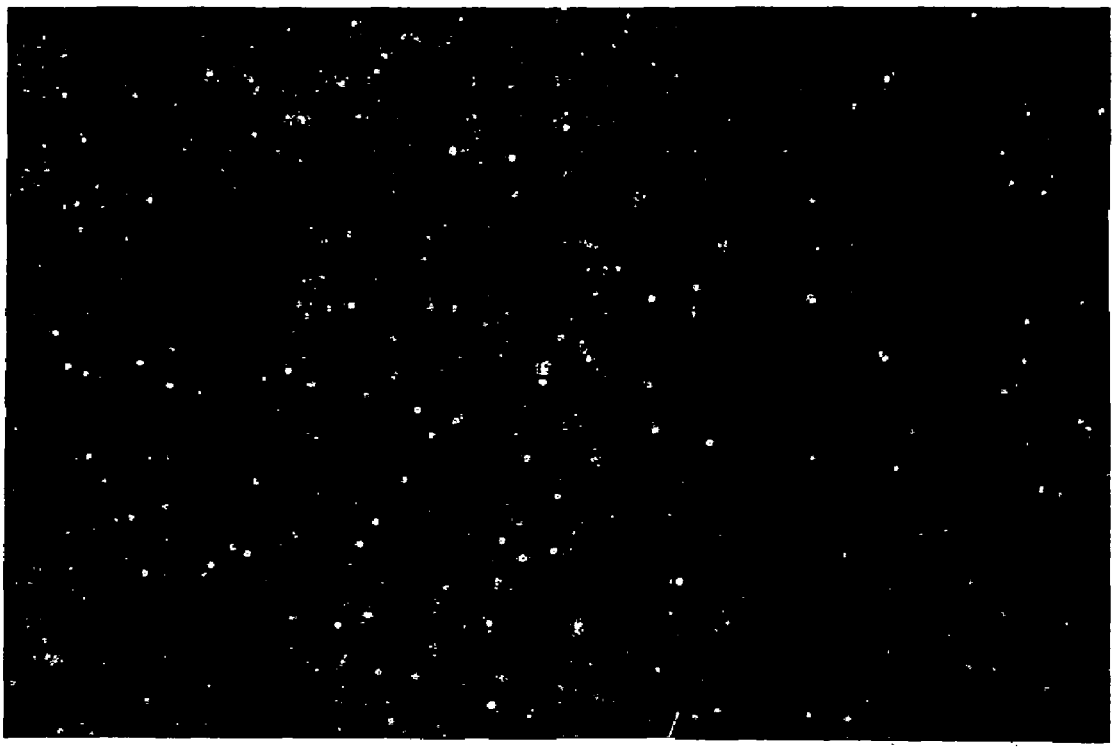
FIGS. 6A and 6B are photographs of cells isolated from the kidney of an adult rat. The newly isolated cells shown in FIG. 6A include undifferentiated spore-like cells (magnification at 100×). After three days in culture, aggregates of cells resembling kidney structures can be (FIG. 6B; magnification at 200×).
Figure 6B:
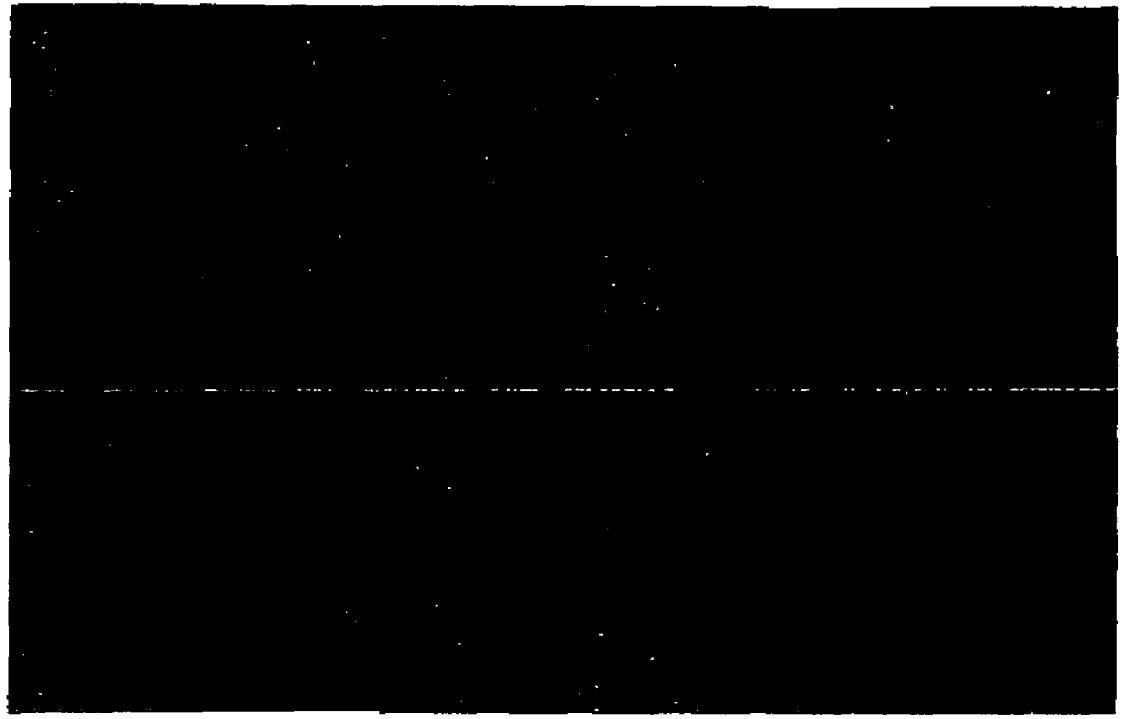

Spore-like cells were isolated from an adult rat kidney according to the protocol described in Example 2. Cells newly isolated from the kidney of an adult rat, which are shown in FIG. 6A, include undifferentiated spore-like cells. After three days in culture, aggregates of cells resembling kidney structures can be seen (FIG. 6B).

Example 7

Spore-like cells were isolated from an adult rat liver according to the protocol described in Example 2. Because the liver is highly vascularized, the intact tissue was washed with PBS. Cells newly isolated from the liver of an adult rat, which are shown in FIGS. 7A and 7C, include undifferentiated spore-like cells. After three days in culture, an aggregate of cells resembling a differentiating liver structure can be seen (FIG. 7B). After seven days in culture, cells resembling hepatocytes can be seen (FIG. 7D).

Example 8

Spore-like cells were isolated from adult mammalian lungs according to the protocol described in Example 2. Spore-like cells were isolated from the lungs of adult rats (see FIGS. 8A-8C) and sheep (see FIG. 8D). The newly isolated cells shown in FIG. 8A include undifferentiated spore-like cells. After six weeks in culture, alveolar-like cells can be seen (FIGS. 8B and 8C). After 30 days in culture, spore-like cells isolated from an adult sheep have formed alveolar-like structures (FIG. 8D) similar to those seen in the lungs of adult cats (FIG. 8E; Histology, F. Hammersen, Ed., Urban & Schwarzenberg, Baltimore-Munich, 1980, FIG. 321).

Example 9

Figure 9A:
FIGS. 9A-9D are photographs of cells isolated from the adrenal gland of an adult rat. Undifferentiated spore-like cells can be seen at Day 0 (see the arrows in FIGS. 9A (200×) and 9B (400×)). After two days in culture, primitive adrenal cells can be seen (FIGS. 9C (200×) and 9D (400×)).
Figure 9B:
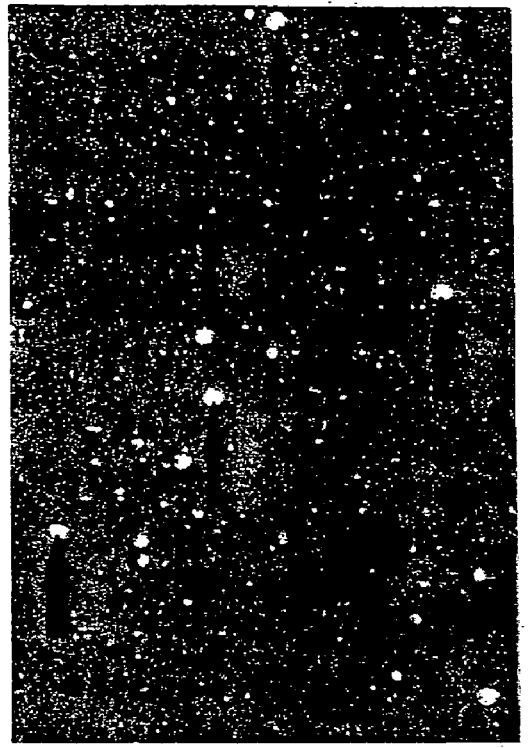
Figure 9C:
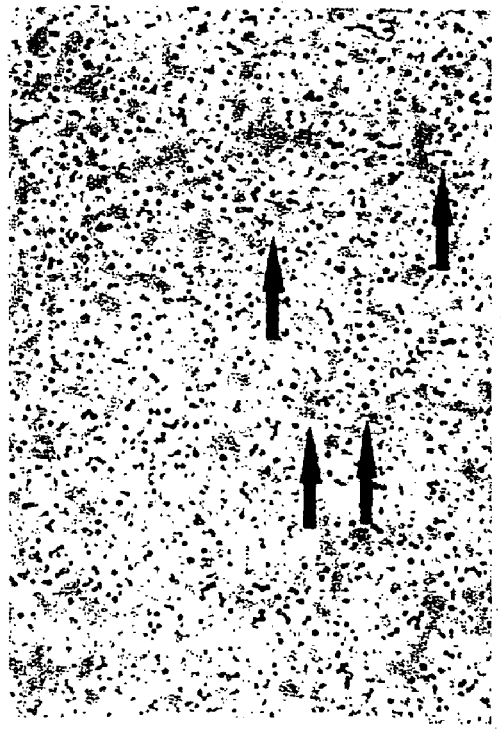
Figure 9D:
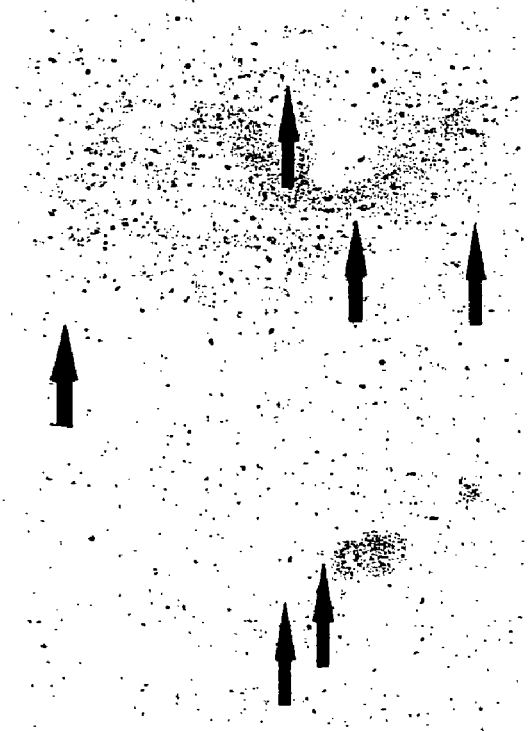

Spore-like cells were isolated from adult rat adrenal glands according to the protocol described in Example 2. Undifferentiated spore-like cells isolated from the adrenal gland of an adult rat can be seen at Day 0 in FIGS. 9A and 9B (see the arrows). After two days in culture, primitive adrenal cells can be seen (FIGS. 9C and 9D).

Example 10

Spore-like cells were isolated from the pancreas of an adult human and from the pancreas of an adult rat. The dissections were carried out in 10% cold fetal serum albumin according to the protocol described in Example 2. Significantly, spore-like cells have been isolated from a portion of the rat pancreas that remained after the islets were removed by ductal injection of collagenase (as described, for example, by Sutton et al., *Transplantation,* 42:689-691, 1986).

Figure 10A:
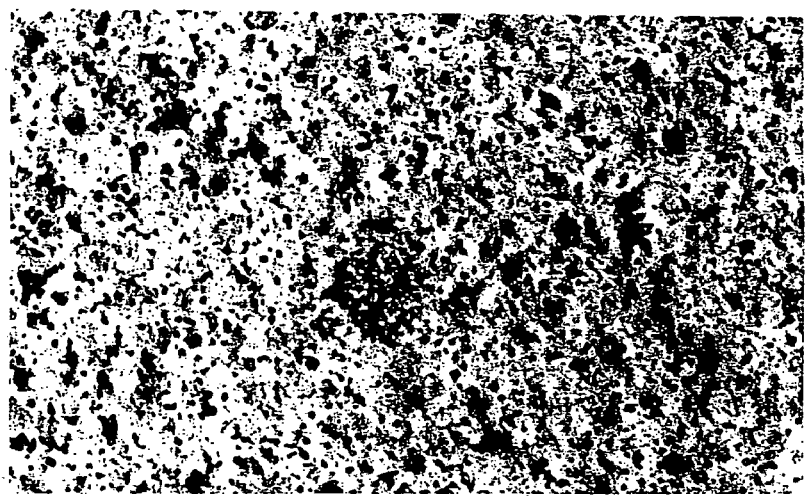
FIGS. 10A-10C are photographs of islet-like structures. These structures formed in cultures of spore-like cells that were isolated from pancreatic tissue that contained no islets (the islets were harvested prior to the isolation of spore-like cells). After six days in culture, more than 100 islet-like structures were present per field (at 100× magnification.
Figure 10B:
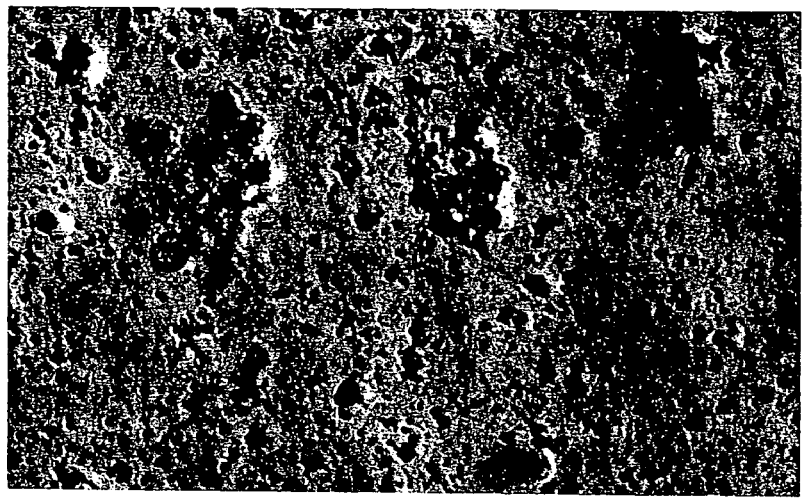
Figure 10C:
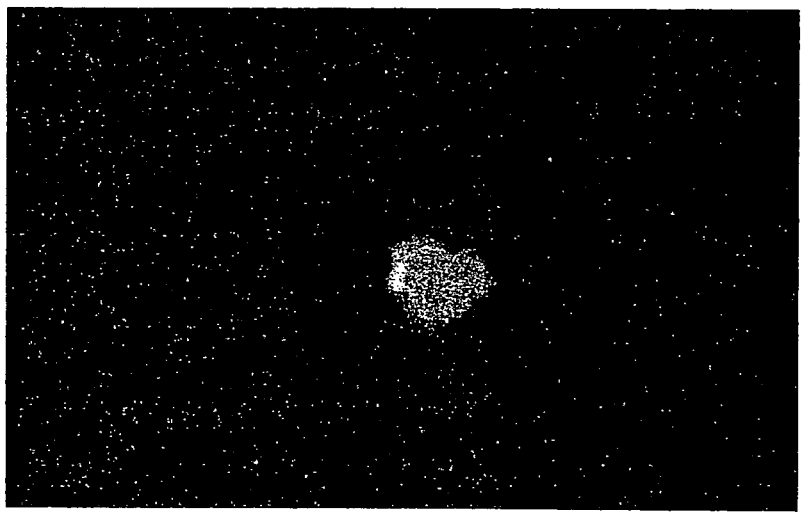

Islet-like structures that formed in cultures of spore-like cells isolated from islet-free pancreatic tissue are shown in FIGS. 10A-10C. After six days in culture, more than 100 islet-like structures were present per field (see FIGS. 10A and 10B), even though the spore-like cells first placed in culture were isolated from a tissue from which the islets had been removed. When the islet-like structures that nevertheless developed were immunostained, insulin expression can be seen (FIG. 10C).

Example 11

Due in part to the unusual appearance of spore-like cells under the light microscope, the cells were examined under an electron microscope. Scanning and electron microscopy was performed according to standard protocols. The electron micrographs revealed several interesting features. For example, the range of spore-like cell sizes may be greater than first appreciated with the light microscope. Some of the spore-like cells shown in FIG. 1A have a diameter of approximately 0.3 microns. The unique cytoarchitecture of the spore-like cell is apparent when viewed with transmission electron microscopy (see FIGS. 2A-2D) or following nuclear staining (such as the 4'6-diamidino-2-phenylindole (DAPI) stain described in Example 12). The interior of the cell is consumed largely with diffuse nuclear material and the cell is surrounded by a "zebra" coating, which is associated with deposits of glycolipids (i.e., carbohydrate and fat). For example, zebra bodies (so-called because of their striped appearance) are associated with mucopolysaccharidoses, such as Hurler's syndrome or with Fabry's disease, in which glycolipids accumulate due to an enzyme deficiency. Spore-like cells thus appear, during at least one stage of their existence, to be unique packets of DNA.

Example 12

A massive accumulation of nuclear material is also apparent when spore-like cells are stained for nucleic acids by methods known to those of ordinary skill in the art. For example, DNA can be stained with either 4'6,-diamidino-2-phenylindole (DAPI) for total DNA staining or with propidium iodide for staining of double-stranded DNA and RNA. DAPI and propidium iodide can be added directly to antifade mounting medium (e.g., 90% glycerol, 1×PBS, and 2.5% 1,4-diazabicyclo[2,2,2]octane (DABCO) (Sigma Chemical Co., St. Louis, Mo.). Spore-like cells stained with DAPI contained a great deal of nuclear material; the ratio of nuclear to cytoplasmic material was much higher in spore-like cells than one would expect in most fully differentiated cell types.

Other Embodiments

One of ordinary skill in the art will appreciate that the spore-like cells described herein can be administered in connection with existing tissue engineering methods, in lieu of differentiated cells in cell-based therapies, and in lieu of cells presently administered following genetic manipulation.

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. An isolated mammalian spore-like cell population, comprising cells that
    are multipotent;
    are approximately one to seven microns in diameter;
    are viable following oxygen-deprivation in a deceased mammal for a period of twenty four hours; and
    have an outer membrane containing one or more dark stripes when viewed by transmission electron microscopy.
2. The spore-like cell population of claim 1, wherein the cells are isolated from the blood of a post-natal mammal by size-exclusion.
3. The spore-like cell population of claim 1, wherein the cells are isolated from the heart, intestine, bladder, kidney, liver, lung, adrenal gland, skin, retina, or pancreas of a post-natal mammal by size-exclusion.
4. The spore-like cell population of claim 1, wherein the cells are isolated from a deceased mammal.
5. The spore-like cell population of claim 1, wherein the cells are approximately one to three microns in diameter.
6. The spore-like cell population of claim 1, wherein the cells are approximately one micron in diameter.
7. The spore-like cell population of claim 1, wherein at least about half the volume of the cells comprises nucleic acids.
8. The spore-like cell population of claim 1, comprising cells that do not express nestin.

* * * * *